United States Patent
Guillemont et al.

(10) Patent No.: US 8,153,640 B2
(45) Date of Patent: Apr. 10, 2012

(54) HIV INHIBITING BICYCLIC PYRIMDINE DERIVATIVES

(75) Inventors: Jerôme Emile Georges Guillemont, Andé (FR); Mikaël Paugam, Heudreville sue eure (FR); Bruno Francois Marie Delest, Rouen (FR); Jan Heeres, Vosselaar (BE); Paulus Joannes Lewi, Turnhout (BE); Paul Adriaan Jan Janssen, Brasschaat (BE); Frank Xavier Jozef Herwig Arts, legal representative, Brasschaat (BE)

(73) Assignee: Tibotec Pharmaceuticals Ltd., Little Island (IE)

( * ) Notice: Subject to any disclaimer, the term of this patent is extended or adjusted under 35 U.S.C. 154(b) by 1170 days.

(21) Appl. No.: 11/718,181

(22) PCT Filed: Oct. 27, 2005

(86) PCT No.: PCT/EP2005/055589
§ 371 (c)(1),
(2), (4) Date: Apr. 27, 2007

(87) PCT Pub. No.: WO2006/045828
PCT Pub. Date: May 4, 2006

(65) Prior Publication Data
US 2008/0085907 A1 Apr. 10, 2008

(51) Int. Cl.
C07D 473/32 (2006.01)
A61K 31/52 (2006.01)
A61P 31/18 (2006.01)
(52) U.S. Cl. ............ 514/263.2; 514/263.4; 544/277
(58) Field of Classification Search ............. 544/277; 514/263.4, 263.2
See application file for complete search history.

(56) References Cited

U.S. PATENT DOCUMENTS
3,459,731 A 8/1969 Gramera et al.

FOREIGN PATENT DOCUMENTS
| DE | 21593 A | 7/1961 |
| EP | 0 834 507 B1 | 4/1998 |
| WO | WO 97/18839 A1 | 5/1997 |
| WO | WO 99/50250 A1 | 10/1999 |
| WO | WO 99/50256 A1 | 10/1999 |
| WO | WO 00/27825 | 5/2000 |
| WO | WO 01/85700 A2 | 11/2001 |
| WO | WO 03/074530 A1 | 9/2003 |
| WO | WO 2004/018473 A2 | 3/2004 |
| WO | WO 2004/065378 A1 | 8/2004 |
| WO | WO 2004/099209 A1 | 11/2004 |
| WO | WO 2005/012304 A2 | 2/2005 |
| WO | WO 2005/012307 A1 | 2/2005 |
| WO | WO 2005/080393 A1 | 9/2005 |
| WO | WO 2005/107760 A1 | 11/2005 |

OTHER PUBLICATIONS

International Search Report for PCT/EP2005/055589 dated Jan. 20, 2006.
Nógrádi, M., et al., "Dimethyl-β-Cyclodextrin", Drugs of the Future, (1984), vol. 9, No. 8, pp. 577-578.

*Primary Examiner* — Susanna Moore

(57) ABSTRACT

HIV replication inhibitors of formula

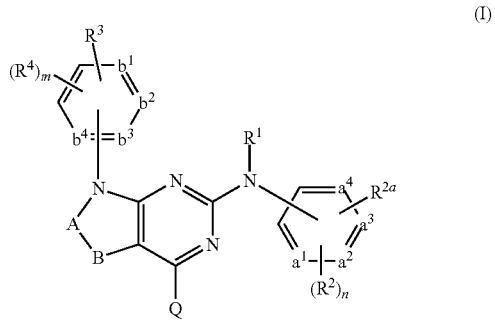

(I)

N-oxides, pharmaceutically acceptable addition salts, quaternary amines or stereoisomeric forms thereof, wherein
-$a^1=a^2$-$a^3=a^4$- is —CH=CH—CH=CH—, —N=CH—CH=CH—, —N=CH—N=CH—, —N=CH—CH=N—, —N=N—CH=CH—; -$b^1=b^2$-$b^3=b^4$- is —CH=CH—CH=CH—, —N=CH—CH=CH—, —N=CH—N=CH—, —N=CH—CH=N—, —N=N—CH=CH—;
n and m is 0, 1, 2, 3 and in certain cases also 4;
$R^1$ is hydrogen; aryl; formyl; $C_{1-6}$alkylcarbonyl; optionally substituted $C_{1-6}$alkyl; $C_{1-6}$alkyloxycarbonyl;
$R^2$ is OH; halo; optionally substituted $C_{1-6}$alkyl, $C_{2-6}$alkenyl or $C_{2-6}$alkynyl; substituted carbonyl; carboxyl; CN; nitro; amino; substituted amino; polyhalomethyl; polyhalomethylthio; —S(=O)$_p$R$^6$; C(=NH)R$^6$;
$R^{2a}$ is CN; amino; substituted amino; optionally substituted $C_{1-6}$alkyl; halo; optionally substituted $C_{1-6}$alkyloxy; substituted carbonyl; —CH=N—NH—C(=O)—R$^{16}$; optionally substituted $C_{1-6}$alkyloxy$C_{1-6}$alkyl; substituted $C_{2-6}$alkenyl or $C_{2-6}$alkynyl; —C(=N—O—R$^8$)—$C_{1-4}$alkyl; $R^7$ or —X—$R^7$;
$R^3$ is CN; amino; $C_{1-6}$alkyl; halo; optionally substituted $C_{1-6}$alkyloxy; substituted carbonyl; —CH=N—NH—C(=O)—R$^{16}$; substituted $C_{1-6}$alkyl; optionally substituted $C_{1-6}$alkyloxy$C_{1-6}$alkyl; substituted $C_{2-6}$alkenyl or $C_{2-6}$alkynyl; —C(=N—O—R$^8$)—$C_{1-4}$alkyl; $R^7$; —X—$R^7$;
$R^4$ is halo; OH; optionally substituted $C_{1-6}$alkyl, $C_{2-6}$alkenyl or $C_{2-6}$alkynyl; $C_{3-7}$cycloalkyl; $C_{1-6}$alkyloxy; CN; nitro; polyhalo$C_{1-6}$alkyl; polyhalo$C_{1-6}$alkyloxy; substituted carbonyl; formyl; amino; mono- or di($C_{1-4}$alkyl)amino or $R^7$;
-A-B— is —CR$^5$=N—, —N=N—, —CH$_2$—CH$_2$—, —CS—NH—, —CO—NH—, —CH=CH—;
pharmaceutical compositions comprising these; methods for the preparation of these compounds and compositions; the use of these compounds for the prevention or the treatment of HIV infection.

18 Claims, No Drawings

HIV INHIBITING BICYCLIC PYRIMDINE DERIVATIVES

CROSS REFERENCE TO RELATED APPLICATIONS

This application is a national stage application of Patent Application No. PCT/EP2005/055589, filed Oct. 27, 2005, which application claims priority from EPO Patent Application No. 04105419.8, filed Oct. 29, 2004, both of which are hereby incorporated by reference in their entirety.

The present invention is concerned with pyrimidine derivatives having HIV (Human Immunodeficiency Virus) replication inhibiting properties. The invention further relates to methods for their preparation and pharmaceutical compositions comprising them. The invention also relates to the use of said compounds in the prevention or the treatment of HIV infection.

Resistance of the HIV virus against currently available HIV drugs continues to be a major cause of therapy failure. This has led to the introduction of combination therapy of two or more anti-HIV agents usually having a different activity profile. Significant progress was made by the introduction of HAART therapy (Highly Active Anti-Retroviral Therapy), which has resulted in a significant reduction of morbidity and mortality in HIV patient populations treated therewith. HAART involves various combinations of nucleoside reverse transcriptase inhibitors (NRTIs), non-nucleoside reverse transcriptase inhibitors (NNRTIs) and protease inhibitors (PIs). Current guidelines for antiretroviral therapy recommend such triple combination therapy regimen for initial treatment. However, these multidrug therapies do not completely eliminate HIV and long-term treatment usually results in multidrug resistance. In particular, half of the patients receiving anti-HIV combination therapy do not respond fully to the treatment, mainly because of resistance of the virus to one or more drugs used. It also has been shown that resistant virus is carried over to newly infected individuals, resulting in severely limited therapy options for these drug-naive patients.

Therefore there is a continued need for new combinations of active ingredients that are effective against HIV. New types of anti-HIV effective active ingredients, differing in chemical structure and activity profile are useful in new types of combination therapy Finding such active ingredients therefore is a highly desirable goal to achieve.

The present invention is aimed at providing particular novel series of bicyclic derivatives having HIV replication inhibiting properties. WO-99/50250, WO-00/27825 and WO-01/85700 disclose certain substituted aminopyrimidines and WO-99/50256 and EP-A-834 507 disclose aminotriazines having HIV replication inhibiting properties. DD-21593 describes a number of bisarylamino substituted purines as compounds having anti-fungal activity.

It now has been found that certain bisaryl substituted bicycles not only act favorably in terms of their capability to inhibit the replication of HIV, but also by their improved ability to inhibit the replication of mutant strains, in particular in strains which have become resistant to one or more known NNRTI drugs (Non Nucleoside Reverse Transcriptase Inhibitor drugs), which strains are referred to as drug or multidrug resistant HIV strains.

The present invention concerns compounds of formula

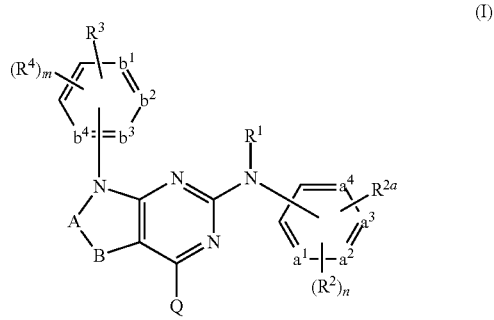

the N-oxides; the pharmaceutically acceptable addition salts; the quaternary amines; or the stereochemically isomeric forms thereof, wherein
-$a^1$=$a^2$-$a^3$=$a^4$- represents a bivalent radical of formula

| | |
|---|---|
| —CH=CH—CH=CH— | (a-1); |
| —N=CH—CH=CH— | (a-2); |
| —N=CH—N=CH— | (a-3); |
| —N=CH—CH=N— | (a-4); |
| —N=N—CH=CH— | (a-5); |

-$b^1$=$b^2$-$b^3$=$b^4$- represents a bivalent radical of formula

| | |
|---|---|
| —CH=CH—CH=CH— | (b-1); |
| —N=CH—CH=CH— | (b-2); |
| —N=CH—N=CH— | (b-3); |
| —N=CH—CH=N— | (b-4); |
| —N=N—CH=CH— | (b-5); | n is 0, 1, 2, 3 and in case -$a^1$=$a^2$-$a^3$=$a^4$- is (a-1), then n may also be 4;
m is 0, 1, 2, 3 and in case -$b^1$=$b^2$-$b^3$=$b^4$- is (b-1), then m may also be 4;
-A-B— represents a bivalent radical of formula

| | |
|---|---|
| —$CR^5$=N— | (c-1); |
| —N=N— | (c-2); |
| —$CH_2$—$CH_2$— | (c-3); |
| —CS—NH— | (c-4); |
| —CO—NH— | (c-5); |

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, or with $C_{1-6}$alkyloxycarbonyl;

each $R^2$ independently is hydroxy; halo; $C_{1-6}$alkyl optionally substituted with one, two or three substituents each independently selected from halo, cyano and —C(=O)$R^6$; $C_{3-7}$cycloalkyl; $C_{2-6}$alkenyl optionally substituted with one, two or three substituents each independently selected from halo, cyano and —C(=O)$R^6$; $C_{2-6}$alkynyl optionally substituted with one, two or three substituents each independently selected from halo, cyano and —C(=O)$R^6$; $C_{1-6}$alkyloxycarbonyl; carboxyl; cyano; nitro; amino; mono- or di($C_{1-6}$alkyl)amino; polyhalomethyl; polyhalomethylthio; —S(=O)$_p$R$^6$; —NH—S(=O)$_p$R$^6$; —C(=O)R$^6$; —NHC(=O)H; —C(=O)NHNH$_2$; NHC(=O)R$^6$; C(=NH)R$^6$;

R$^{2a}$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; C(=O)—NHR$^{13}$; C(=O)—NR$^{13}$R$^{14}$; —C(=O)R$^{15}$; —CH=N—NH—C(=O)—R$^{16}$; C$_{1-6}$alkyl substituted with one, two or three substituents each independently selected from halo, cyano, NR$^9$R$^{10}$, —C(=O)—NR$^9$R$^{10}$, —C(=O)—C$_{1-6}$alkyl or R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one, two or three substituents each independently selected from halo, cyano, NR$^9$R$^{10}$, —C(=O)—NR$^9$R$^{10}$, —C(=O)—C$_{1-6}$alkyl and R$^7$; C$_{2-6}$alkenyl substituted with one, two or three substituents each independently selected from halo, cyano, NR$^9$R$^{10}$, —C(=O)—NR$^9$R$^{10}$, —C(=O)—C$_{1-6}$alkyl and R$^7$; C$_{2-6}$alkynyl substituted with one, two or three substituents each independently selected from halo, cyano, NR$^9$R$^{10}$, —C(=O)—NR$^9$R$^{10}$, —C(=O)—C$_{1-6}$alkyl and R$^7$; —C(=N—O—R$^8$)—C$_{1-4}$alkyl; R$^7$ or —X—R$^7$;

R$^3$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one, two or three substituents each independently selected from halo, cyano, NR$^9$R$^{10}$, —C(=O)—NR$^9$R$^{10}$, —C(=O)—C$_{1-6}$alkyl and R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl and R$^7$; C$_{1-6}$alkyloxyC$_{1-6}$alkyl optionally substituted with one, two or three substituents each independently selected from halo, cyano, NR$^9$R$^{10}$, —C(=O)—NR$^9$R$^{10}$, —C(=O)—C$_{1-6}$alkyl and R$^7$; C$_{2-6}$alkenyl substituted with one, two or three substituents each independently selected from halo, cyano, NR$^9$R$^{10}$, —C(=O)—NR$^9$R$^{10}$, —C(=O)—C$_{1-6}$alkyl and R$^7$; C$_{2-6}$alkynyl substituted with one, two or three substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ and —X—R$^7$;

X is —NR$^1$—, —O—, —C(=O)—, —S—, —S(=O)$_p$—;

each R$^4$ independently is halo; hydroxy; C$_{1-6}$alkyl optionally substituted with one, two or three substituents each independently selected from halo, cyano and —C(=O)R$^6$; C$_{2-6}$alkenyl optionally substituted with one, two or three substituents each independently selected from halo, cyano and —C(=O)R$^6$; C$_{2-6}$alkynyl optionally substituted with one, two or three substituents each independently selected from halo, cyano and —C(=O)R$^6$; C$_{3-7}$cycloalkyl; C$_{1-6}$alkyloxy; cyano; nitro; polyhalo-C$_{1-6}$alkyl; polyhaloC$_{1-6}$alkyloxy; aminocarbonyl; mono- or di(C$_{1-4}$alkyl)amino-carbonyl; C$_{1-6}$alkyloxycarbonyl; C$_{1-6}$alkylcarbonyl; formyl; amino; mono- or di(C$_{1-4}$alkyl)amino or R$^7$;

Q is hydrogen, C$_{1-6}$alkyl, halo, polyhaloC$_{1-6}$alkyl, or —NR$^9$R$^{10}$;

R$^5$ is hydrogen, C$_{1-6}$alkyl, aryl, pyridyl, thienyl, furanyl, amino, mono- or di(C$_{1-4}$alkyl)amino;

R$^6$ is C$_{1-4}$alkyl, amino, mono- or di(C$_{1-4}$alkyl)amino or polyhaloC$_{1-4}$alkyl;

R$^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxy C$_{1-6}$alkyl, aminoC$_{1-6}$alkyl, mono and di(C$_{1-6}$alkyl)amino C$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$), R$^{7a}$, —X—R$^{7a}$ and R$^{7a}$—C$_{1-4}$alkyl;

R$^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)amino C$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl and —CH(=N—O—R$^8$);

R$^8$ is hydrogen, C$_{1-4}$alkyl, aryl or arylC$_{1-4}$alkyl;

R$^9$ and R$^{10}$ each independently are hydrogen; hydroxy; C$_{1-6}$alkyl; C$_{1-6}$alkyloxy; C$_{1-6}$alkyl-carbonyl; C$_{1-6}$alkyloxycarbonyl; amino; mono- or di(C$_{1-6}$alkyl)amino; mono- or di(C$_{1-6}$alkyl)aminocarbonyl; —CH(=NR$^{11}$) or R$^7$, wherein each of the aforementioned C$_{1-6}$alkyl groups may optionally and each individually be substituted with one or two substituents each independently selected from hydroxy, C$_{1-6}$alkyloxy, hydroxy-C$_{1-6}$alkyloxy, carboxyl, C$_{1-6}$alkyloxycarbonyl, cyano, amino, imino, mono- and di(C$_{1-4}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, R$^7$; or R$^9$ and R$^{10}$ may be taken together to form a bivalent or trivalent radical of formula

| | |
|---|---|
| —CH$_2$—CH$_2$—CH$_2$—CH$_2$— | (d-1) |
| —CH$_2$—CH$_2$—CH$_2$—CH$_2$—CH$_2$— | (d-2) |
| —CH$_2$—CH$_2$—O—CH$_2$—CH$_2$— | (d-3) |
| —CH$_2$—CH$_2$—S—CH$_2$—CH$_2$— | (d-4) |
| —CH$_2$—CH$_2$—NR$^{12}$—CH$_2$—CH$_2$— | (d-5) |
| —CH$_2$—CH=CH—CH$_2$— | (d-6) |
| =CH—CH=CH—CH=CH— | (d-7) |

R$^{11}$ is cyano; C$_{1-4}$alkyl optionally substituted with C$_{1-4}$alkyloxy, cyano, amino, mono- or di(C$_{1-4}$alkyl)amino or aminocarbonyl; C$_{1-4}$alkylcarbonyl; C$_{1-4}$alkyloxycarbonyl; aminocarbonyl; mono- or di(C$_{1-4}$alkyl)aminocarbonyl;

R$^{12}$ is hydrogen or C$_{1-4}$alkyl;

R$^{13}$ and R$^{14}$ each independently are C$_{1-6}$alkyl optionally substituted with cyano or aminocarbonyl, C$_{2-6}$alkenyl optionally substituted with cyano or aminocarbonyl, C$_{2-6}$alkynyl optionally substituted with cyano or aminocarbonyl;

R$^{15}$ is C$_{1-6}$alkyl substituted with cyano or aminocarbonyl;

R$^{16}$ is C$_{1-6}$alkyl optionally substituted with cyano or aminocarbonyl, or R$^7$;

each p is 1 or 2;

each aryl is phenyl or phenyl substituted with one, two, three, four or five substituents each independently selected from halo, hydroxy, mercapto, C$_{1-6}$alkyl, hydroxy-C$_{1-6}$alkyl, aminoC$_{1-6}$alkyl, mono or di(C$_{1-6}$alkyl)aminoC$_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, a radical Het and —X-Het;

Het is pyridyl, thienyl, furanyl, oxazolyl, isoxazolyl, imidazolyl, pyrazolyl, thiazolyl, thiadiazolyl, oxadiazolyl quinolinyl, benzothienyl, benzofuranyl; which each may optionally be substituted with one or two $C_{1-4}$alkyl radicals.

The present invention also relates to the use of a compound for the manufacture of a medicament for the treatment or prevention of HIV infection, wherein the compound belongs to the group of compounds having the formula (I) or any of the subgroups of compounds as specified herein.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{1-2}$alkyl defines methyl and ethyl; $C_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like. Preferred amongst $C_{2-6}$alkenyl and $C_{2-6}$alkynyl are the unsaturated analogs having from 2 to 4 carbon atoms, i.e. $C_{2-4}$alkenyl and $C_{2-4}$alkynyl respectively. Any $C_{2-6}$alkenyl or $C_{2-6}$alkynyl linked to a heteroatom preferably is connected to said heteroatom by a saturated carbon atom.

In a number of instances the radicals $C_{1-6}$alkynyl, $C_{2-6}$alkenyl, or $C_{2-6}$alkynyl may be substituted with one, two or three substituents. Preferably, said radicals are substituted with up to 2 substituents, more preferably with one substituent.

A monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclo propyl, cyclobutyl, cyclopentyl, cyclohexyl, cycloheptyl, cyclooctyl, bicyclo[4,2,0]-octanyl, cyclononanyl, cyclodecanyl, decahydronapthalenyl, tetradecahydroanthracenyl and the like. Preferred are cyclopropyl, cyclobutyl, cyclopentyl, cyclohexyl, cycloheptyl; more preferred are cyclopentyl, cyclohexyl, cycloheptyl.

Particular examples of monocyclic, bicyclic or tricyclic partially saturated carbocycles are cyclopropenyl, cyclobutenyl, cyclopentenyl, cyclohexenyl, cycloheptenyl, cyclooctenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydro-anthracenyl and the like.

Particular examples of monocyclic, bicyclic or tricyclic aromatic carbocycles are phenyl, naphthalenyl, anthracenyl. Preferred is phenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydro-thienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydro-quinolinyl, octahydroindolyl and the like. Preferred are tetrahydrofuranyl, pyrrolidinyl, dioxolanyl, imidazolidinyl, thiazolidinyl, dihydrooxazolyl, triazolidinyl, piperidinyl, dioxanyl, morpholinyl, thiomorpholinyl, piperazinyl. Particularly preferred are tetrahydrofuranyl, pyrrolidinyl, dioxolanyl, piperidinyl, dioxanyl, morpholinyl, thiomorpholinyl, piperazinyl.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like. Preferred are pyrrolinyl, imidazolinyl, 2,3-dihydrobenzofuranyl, 1,3-benzodioxolyl, indolinyl.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzo-thienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzo-thiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolo-pyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolo-pyrazinyl, thiadiazolopyrazinyl, triazolopyrazinyl, oxadiazolopyrimidinyl, thiadiazolo-pyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolo-triazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

Preferred aromatic heterocycles are monocyclic or bicyclic aromatic heterocycles. Interesting monocyclic, bicyclic or tricyclic aromatic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, carbazolyl, acridinyl, phenothiazinyl, phenoxazinyl and the like.

Particularly interesting aromatic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The terms carboxyl, carboxy or hydroxycarbonyl refer to a group —COOH.

The term halo is generic to fluoro, chloro, bromo and iodo. As used in the foregoing and hereinafter, polyhalomethyl as a group or part of a group is defined as mono- or polyhalo-substituted methyl, in particular methyl with one or more fluoro atoms, for example, difluoromethyl or trifluoromethyl; polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, the groups defined in halomethyl, 1,1-difluoro-ethyl and the like. In case more than one halogen atoms are attached to an alkyl group within the definition of polyhalo-methyl, polyhalo$C_{1-4}$alkyl or polyhalo$C_{1-6}$alkyl, they may be the same or different.

Whenever it occurs in the definition of the compounds of formula (I) or in any of the subgroups specified herein, each aryl independently is as defined above in the definition of the compounds of formulas (I) or each aryl can have any of the meanings specified hereinafter.

The term heterocycle in the definition of $R^7$ or $R^{7a}$ is meant to include all the possible isomeric forms of the heterocycles, for instance, pyrrolyl comprises 1H-pyrrolyl and 2H-pyrrolyl.

The carbocycle or heterocycle in the definition of $R^7$ or $R^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (e.g. $R^7$) occurs more than one time in any constituent, each definition of such variable is independent.

Any of the restrictions in the definitions of the radicals herein are meant to be applicable to the group of compounds of formula (I) as well as to any subgroup defined or mentioned herein.

Lines drawn from substituents into ring systems indicate that the bond may be attached to any of the suitable ring atoms.

For therapeutic use, salts of the compounds of formula (I) are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form. The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art. Stereochemically isomeric forms of the compounds of formula (I) are intended to be embraced within the scope of this invention.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I), which are stereochemically pure.

Particular subgroups of compounds of formula (I) or any of the subgroups of compounds of formula (I) specified herein which are the non-salt-forms, the salts, the N-oxide forms and stereochemically isomeric forms. Of interest amongst these are the non-salt-forms, the salts and stereochemically isomeric forms. As used herein, the term 'non-salt-form' refers to the form of a compound which is not a salt, which in most cases will be the free base form.

It is to be understood that any of the subgroups of compounds of formulae (I) as defined herein, are meant to also comprise any prodrugs, N-oxides, addition salts, quaternary amines, metal complexes and stereochemically isomeric forms of such compounds.

Whenever mention is made hereinbefore or hereinafter that substituents can be selected each independently out of a list of numerous definitions, such as for example for $R^9$ and $R^{10}$, all possible combinations are intended which are chemically possible or which lead to chemically stable molecules.

A number of subgroups of compounds of formula (I) are defined hereinafter. Further subgroups of compounds of formula (I) that form part of the disclosure of this invention may comprise permutations of any of the definitions used to specify the subgroups defined hereinafter.

Of interest are those compounds of formula (I), or any subgroup of compounds of formula (I) specified herein, wherein the compounds are other than 2-p-toluidino-6-methyl-9-p-toluoyl-purine and 2-p-phenetidino-6-methyl-9-p-ethoxyphenylpurine.

Of interest are those compounds of formula (I), or any subgroup of compounds of formula (I) specified herein, wherein $R^{2a}$ is other than methyl or ethoxy; or wherein $R^{2a}$ is other than $C_{1-2}$alkyl or $C_{1-2}$alkyloxy; $R^{2a}$ is other than $C_{1-4}$alkyl or $C_{1-4}$alkyloxy; or wherein $R^{2a}$ is other than $C_{1-6}$alkyl or $C_{1-6}$alkyloxy. Also of interest are those compounds of formula (I), or any subgroup of compounds of formula (I) specified herein, wherein $R^3$ is other than methyl or ethoxy; or wherein $R^3$ is other than $C_{1-2}$alkyl or $C_{1-2}$alkyloxy; $R^{2a}$ is other than $C_{1-4}$alkyl or $C_{1-4}$alkyloxy; or wherein $R^3$ is other than $C_{1-6}$alkyl or $C_{1-6}$alkyloxy.

Also of interest are those compounds of formula (I), or any subgroup of compounds of formula (I) specified herein, wherein $R^{2a}$ and $R^3$ is other than methyl or ethoxy; or wherein $R^{2a}$ and $R^3$ are other than $C_{1-2}$alkyl or $C_{1-2}$alkyloxy; or wherein $R^{2a}$ and $R^3$ are other than $C_{1-4}$alkyl or $C_{1-4}$alkyloxy; or wherein $R^{2a}$ and $R^3$ are other than $C_{1-6}$alkyl or $C_{1-6}$alkyloxy.

Particular subgroups of the compounds of formula (I) are those compounds of formula (I), or any subgroup of compounds of formula (I) specified herein, wherein -$a^1$=$a^2$-$a^3$=$a^4$- is —CH=CH—CH=CH— (a-1).

Further subgroups of the compounds of formula (I) are those compounds of formula (I), or any subgroup of compounds of formula (I) specified herein, wherein -$b^1$=$b^2$-$b^3$=$b^4$- is —CH=CH—CH=CH— (b-1).

Further subgroups of the compounds of formula (I) are those compounds of formula (I), or any subgroup of compounds of formula (I) specified herein, wherein (a) n is 0, 1, 2, 3; or wherein (b) n is 0, 1 or 2; or (c) n is 0.

Other subgroups of the compounds of formula (I) are those compounds of formula (I), or any subgroup of compounds of formula (I) specified herein, wherein (a) m is 0, 1, 2, 3; or wherein (b) m is 0, 1 or 2; or (c) m is 2.

Still further subgroups of the compounds of formula (I) are those compounds of formula (I), or any subgroup of compounds of formula (I) specified herein, wherein
(a) $R^1$ is hydrogen; formyl; $C_{1-6}$alkylcarbonyl; $C_{1-6}$alkyl; $C_{1-6}$alkyloxycarbonyl; or
(b) $R^1$ is hydrogen; $C_{1-6}$alkyl; or
(c) $R^1$ is hydrogen.

Still further subgroups of the compounds of formula (I) are those compounds of formula (I), or any subgroup of compounds of formula (I) specified herein, wherein
(a) $R^2$ is hydroxy; halo; $C_{1-6}$alkyl optionally substituted with one substituent selected from halo, cyano and —C(=O) $R^6$; $C_{3-7}$cycloalkyl; $C_{2-6}$alkenyl optionally substituted with one substituent selected from halo, cyano and —C(=O) $R^6$; $C_{2-6}$alkynyl optionally substituted with one substituent selected from halo, cyano and —C(=O)R$^6$; C$_{1-6}$alkyloxycarbonyl; carboxyl; cyano; nitro; amino; mono- or di(C$_{1-6}$alkyl)amino; polyhalomethyl; polyhalomethylthio; —S(=O)$_p$R$^6$; —NH—S(=O)$_p$R$^6$; —C(=O)R$^6$; —NHC(=O)H; —C(=O)NHNH$_2$; NHC(=O)R$^6$; C(=NH)R$^6$;

(b) R$^2$ is hydroxy; halo; C$_{1-6}$alkyl optionally substituted with one substituent selected from halo, cyano and —C(=O)R$^6$; C$_{2-6}$alkenyl optionally substituted with one substituent selected from halo, cyano and —C(=O)R$^6$; C$_{2-6}$alkynyl optionally substituted with one substituent selected from halo, cyano and —C(=O)R$^6$; C$_{1-6}$alkyloxycarbonyl; carboxyl; cyano; nitro; amino; mono- or di(C$_{1-6}$alkyl)amino; trifluoromethyl;

(c) R$^2$ is halo, C$_{1-6}$alkyl optionally substituted with cyano, C$_{2-6}$alkenyl optionally substituted with cyano, C$_{2-6}$alkynyl optionally substituted with cyano, C$_{1-6}$alkyloxy-carbonyl, carboxyl, cyano, amino, mono(C$_{1-6}$alkyl)amino, di(C$_{1-6}$alkyl)amino;

(d) R$^2$ is halo, cyano, aminocarbonyl, C$_{1-6}$alkyloxy, C$_{1-6}$alkyl, C$_{1-6}$alkyl substituted with cyano or C$_{2-6}$alkenyl substituted with cyano;

(e) R$^2$ is halo, cyano, aminocarbonyl, C$_{1-4}$alkyl substituted with cyano or C$_{2-4}$alkenyl substituted with cyano;

(f) R$^2$ is cyano, aminocarbonyl; or (g) R$^2$ is cyano.

Still further subgroups of the compounds of formula (I) are those compounds of formula (I), or any subgroup of compounds of formula (I) specified herein, wherein (a) R$^{2a}$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one substituent selected from halo, cyano, NR$^9$R$^{10}$, —C(=O)—NR$^9$R$^{10}$, —C(=O)—C$_{1-6}$alkyl and R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one substituent selected from halo, cyano, NR$^9$R$^{10}$, —C(=O)—NR$^9$R$^{10}$, —C(=O)—C$_{1-6}$alkyl and R$^7$; C$_{2-6}$alkenyl substituted with one substituent selected from halo, cyano, NR$^9$R$^{10}$, —C(=O)—NR$^9$R$^{10}$, —C(=O)—C$_{1-6}$alkyl and R$^7$; C$_{2-6}$alkynyl substituted with one substituent selected from halo, cyano, NR$^9$R$^{10}$, —C(=O)—NR$^9$R$^{10}$, —C(=O)—C$_{1-6}$alkyl and R$^7$; —C(=N—O—R$^8$)—C$_{1-4}$alkyl; R$^7$ or —X—R$^7$;

(b) R$^{2a}$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one substituent selected from halo, cyano, —C(=O)—NR$^9$R$^{10}$; C$_{1-6}$alkyl substituted with hydroxy and a second substituent selected from halo, cyano, —C(=O)—NR$^9$R$^{10}$; C$_{1-6}$alkyloxyC$_{1-6}$alkyl optionally substituted with one substituent selected from halo, cyano, —C(=O)—NR$^9$R$^{10}$; C$_{2-6}$alkenyl substituted with one substituent selected from halo, cyano, —C(=O)—NR$^9$R$^{10}$; C$_{2-6}$alkynyl substituted with one substituent selected from halo, cyano, —C(=O)—NR$^9$R$^{10}$;

(c) R$^{2a}$ is halo, cyano, aminocarbonyl, C$_{1-6}$alkyl optionally substituted with cyano or aminocarbonyl, C$_{2-6}$alkenyl optionally substituted with cyano or aminocarbonyl;

(d) R$^{2a}$ is halo, cyano, aminocarbonyl, C$_{1-6}$alkyl substituted with cyano or aminocarbonyl, or C$_{2-6}$alkenyl substituted with cyano or aminocarbonyl;

(e) R$^{2a}$ is cyano, aminocarbonyl, C$_{1-6}$alkyl substituted with cyano or C$_{2-6}$alkenyl substituted with cyano;

(f) R$^{2a}$ is cyano, aminocarbonyl, C$_{1-4}$alkyl substituted with cyano or C$_{2-4}$alkenyl substituted with cyano;

(g) R$^{2a}$ is cyano, C$_{1-4}$alkyl substituted with cyano or C$_{2-4}$alkenyl substituted with cyano; or (h) R$^{2a}$ is cyano.

Still other subgroups of the compounds of formula (I) are those compounds of formula (I), or any subgroup of compounds of formula (I) specified herein, wherein (a) -A-B— represents a bivalent radical of formula —CR$^5$=N—  (c-1);

—N=N—  (c-2);

—CH$_2$—CH$_2$—  (c-3);

—CH=CH—  (c-6);

(b) -A-B— represents a bivalent radical of formula

—CR$^5$=N—  (c-1);

(c) -A-B— represents a bivalent radical of formula

—N=N—  (c-2);

(d) -A-B— represents a bivalent radical of formula

—CH$_2$—CH$_2$—  (c-3);

(e) -A-B— represents a bivalent radical of formula

—CS—NH—  (c-4);

(f) -A-B— represents a bivalent radical of formula

—CO—NH— (c-5);

(g) -A-B— represents a bivalent radical of formula

—CH=CH—  (c-6);

(h) -A-B— represents a bivalent radical of formula —CH=N—.

Still other subgroups of the compounds of formula (I) are those compounds of formula (I), or any subgroup of compounds of formula (I) specified herein, wherein (a) R$^3$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one substituent selected from halo, cyano, NR$^9$R$^{10}$, —C(=O)—NR$^9$R$^{10}$, —C(=O)—C$_{1-6}$alkyl and R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl and R$^7$; C$_{1-6}$alkyloxyC$_{1-6}$alkyl optionally substituted with one substituent selected from halo, cyano, NR$^9$R$^{10}$, —C(=O)—NR$^9$R$^{10}$, —C(=O)—C$_{1-6}$alkyl and R$^7$; C$_{2-6}$alkenyl substituted with one substituent selected from halo, cyano, NR$^9$R$^{10}$, —C(=O)—NR$^9$R$^{10}$, —C(=O)—C$_{1-6}$alkyl and R$^7$; C$_{2-6}$alkynyl substituted with one substituent selected from halo, cyano, NR$^9$R$^{10}$, —C(=O)—NR$^9$R$^{10}$, —C(=O)—C$_{1-6}$alkyl and R$^7$; —C(=N—O—R$^8$)—C$_{1-4}$alkyl; R$^7$ or —X—R$^7$;

(b) R$^3$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one substituent selected from halo, cyano, —C(=O)—NR$^9$R$^{10}$; C$_{1-6}$alkyl substituted with hydroxy and a second substituent selected from halo, cyano, —C(=O)—NR$^9$R$^{10}$; C$_{1-6}$alkyloxyC$_{1-6}$alkyl optionally substituted with one substituent selected from halo, cyano, —C(=O)—NR$^9$R$^{10}$; C$_{2-6}$alkenyl substituted with one substituent selected from halo, cyano, —C(=O)—NR$^9$R$^{10}$; C$_{2-6}$alkynyl substituted with one substituent selected from halo, cyano, —C(=O)—NR$^9$R$^{10}$;

(c) R$^3$ is halo, cyano, aminocarbonyl, C$_{1-6}$alkyl optionally substituted with cyano or aminocarbonyl, C$_{2-6}$alkenyl optionally substituted with cyano or aminocarbonyl;

(d) R$^3$ is halo, cyano, aminocarbonyl, C$_{1-6}$alkyl substituted with cyano or amino-carbonyl, or C$_{2-6}$alkenyl substituted with cyano or aminocarbonyl;

(e) R$^3$ is cyano, C$_{1-4}$alkyl substituted with cyano or C$_{2-4}$alkenyl substituted with cyano;

(f) R$^3$ is C$_{1-4}$alkyl substituted with cyano or C$_{2-4}$alkenyl substituted with cyano;

(g) R$^3$ is C$_{2-4}$alkyl substituted with cyano or C$_{2-4}$alkenyl substituted with cyano;

(h) R$^3$ is C$_{2-4}$alkenyl substituted with cyano;

(i) R$^3$ is ethenyl substituted with cyano;

(j) R$^3$ is (E)-2-cyanoethenyl.

Still further subgroups of the compounds of formula (I) are those compounds of formula (I), or any subgroup of compounds of formula (I) specified herein, wherein (a) R$^4$ is halo; hydroxy; C$_{1-6}$alkyl optionally substituted with one substituent selected from halo, cyano or —C(=O)R$^6$; C$_{2-6}$alkenyl optionally substituted with one substituent selected from halo, cyano or —C(=O)R$^6$; C$_{2-6}$alkynyl optionally substituted with one substituent selected from halo, cyano or —C(=O)R$^6$; C$_{3-7}$cycloalkyl; C$_{1-6}$alkyloxy; cyano; nitro; polyhaloC$_{1-6}$alkyl; polyhaloC$_{1-6}$alkyloxy; aminocarbonyl; mono- or di(C$_{1-4}$alkyl)aminocarbonyl; C$_{1-6}$alkyloxycarbonyl; C$_{1-6}$alkylcarbonyl; formyl; amino; mono- or di(C$_{1-4}$alkyl)amino or R$^7$;

(b) R$^4$ is halo; hydroxy; C$_{1-6}$alkyl optionally substituted with one substituent selected from cyano; C$_{2-6}$alkenyl optionally substituted with cyano; C$_{2-6}$alkynyl optionally substituted with cyano; C$_{3-7}$cycloalkyl; C$_{1-6}$alkyloxy; cyano; nitro; trifluoromethyl; aminocarbonyl; mono- or di(C$_{1-4}$alkyl)aminocarbonyl; C$_{1-6}$alkyloxycarbonyl; C$_{1-6}$alkylcarbonyl; formyl; amino; mono- or di(C$_{1-4}$alkyl)amino and R$^7$;

(c) R$^4$ is halo; hydroxy; C$_{1-6}$alkyl optionally substituted with cyano; C$_{2-6}$alkenyl optionally substituted with cyano; C$_{2-6}$alkynyl optionally substituted with cyano; C$_{1-6}$alkyloxy; cyano; nitro; trifluoromethyl; aminocarbonyl; mono- or di(C$_{1-4}$alkyl)aminocarbonyl; C$_{1-6}$alkyloxycarbonyl; C$_{1-6}$alkylcarbonyl; formyl; amino; mono- or di(C$_{1-4}$alkyl)amino;

(d) R$^4$ is halo, hydroxy, C$_{1-6}$alkyl, C$_{2-6}$alkenyl, C$_{2-6}$alkynyl, C$_{1-6}$alkyloxy, cyano, nitro, amino;

(e) R$^4$ is halo, hydroxy, C$_{1-4}$alkyl, C$_{1-4}$alkyloxy, cyano; or (f) R$^4$ is halo, C$_{1-4}$alkyl, C$_{1-4}$alkyloxy.

Still further subgroups of the compounds of formula (I) are those compounds of formula (I), or any subgroup of compounds of formula (I) specified herein, wherein (a) R$^5$ is hydrogen, C$_{1-6}$alkyl, aryl, pyridyl, thienyl, furanyl;

(b) R$^5$ is hydrogen, C$_{1-6}$alkyl, aryl, pyridyl, furanyl; wherein aryl in (a) or (b) may have the meanings defined hereinabove or hereinafter.

Still further subgroups of the compounds of formula (I) are those compounds of formula (I), or any subgroup of compounds of formula (I) specified herein, wherein (a) Q is hydrogen, C$_{1-6}$alkyl or —NR$^9$R$^{10}$;

(b) Q is hydrogen or —NR$^9$R$^{10}$;

(c) Q is hydrogen, amino, mono- or di-C$_{1-4}$alkylamino; (d) Q is hydrogen or C$_{1-6}$alkyl; or (d) Q is hydrogen.

Other subgroups of the compounds of formula (I) are those compounds of formula (I), or any subgroup of compounds of formula (I) specified herein, wherein (a) R$^6$ is C$_{1-4}$alkyl, amino, mono- or di(C$_{1-4}$alkyl)amino; in particular (b) R$^6$ is C$_{1-4}$alkyl or amino; or (c) R$^6$ is C$_{1-4}$alkyl.

Still further subgroups of the compounds of formula (I) are those compounds of formula (I), or any subgroup of compounds of formula (I) specified herein, wherein (a) R$^7$ is a monocyclic or bicyclic, partially saturated or aromatic carbocycle or a monocyclic or bicyclic, partially saturated or aromatic heterocycle, wherein each of said carbocyclic or heterocyclic ring systems may optionally be substituted with one, two or three substituents each independently selected from halo, hydroxy, mercapto, C$_{1-6}$alkyl, hydroxyC$_{1-6}$alkyl, aminoC$_{1-6}$alkyl, C$_{1-6}$alkylcarbonyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy and aminocarbonyl; in particular (b) R$^7$ is any of the specific monocyclic or bicyclic, partially saturated or aromatic carbocycles or monocyclic or bicyclic, partially saturated or aromatic heterocycles specifically mentioned in this specification, wherein each of said carbocyclic or heterocyclic ring systems may optionally be substituted with one, two or three substituents each independently selected from halo, hydroxy, mercapto, C$_{1-6}$alkyl, hydroxyC$_{1-6}$alkyl, aminoC$_{1-6}$alkyl, C$_{1-6}$alkylcarbonyl, C$_{1-6}$alkyloxy, C$_{1-6}$alkyloxy-carbonyl, C$_{1-6}$alkylthio, cyano, nitro, polyhaloC$_{1-6}$alkyl, polyhaloC$_{1-6}$alkyloxy and aminocarbonyl;

(c) R$^{7a}$ is a monocyclic or bicyclic, partially saturated or aromatic carbocycle or a monocyclic or bicyclic, partially saturated or aromatic heterocycle, wherein each of said carbocyclic or heterocyclic ring systems may optionally be substituted with one, two or three substituents each independently selected from halo, hydroxy, mercapto, C$_{1-6}$alkyl, hydroxyC$_{1-6}$alkyl, aminoC$_{1-6}$alkyl, C$_{1-6}$alkylcarbonyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy and aminocarbonyl; in particular (d) R$^{7a}$ is any of the specific monocyclic or bicyclic, partially saturated or aromatic carbocycles or monocyclic or bicyclic, partially saturated or aromatic heterocycles specifically mentioned in this specification, wherein each of said carbocyclic or heterocyclic ring systems may optionally be substituted with one, two or three substituents each independently selected from halo, hydroxy, mercapto, C$_{1-6}$alkyl, hydroxyC$_{1-6}$alkyl, aminoC$_{1-6}$alkyl, C$_{1-6}$alkylcarbonyl, C$_{1-6}$alkyloxy, C$_{1-6}$alkyloxy-carbonyl, C$_{1-6}$alkylthio, cyano, nitro, polyhaloC$_{1-6}$alkyl, polyhaloC$_{1-6}$alkyloxy and aminocarbonyl.

Further subgroups of the compounds of formula (I) are those compounds of formula (I), or any subgroup of compounds of formula (I) specified herein, wherein (a) X is —NR$^1$—, —O— or —S—;

(b) (b) X is —NR$^1$- or —O—;

(c) (c) X is —NH—, —N(C$_{1-4}$alkyl)-, —O—;

(d) X is —NH—, —N(CH$_3$)—, —O—; or (e) X is —NH—, —O—.

Other subgroups of the compounds of formula (I) are those compounds of formula (I), or any subgroup of compounds of formula (I) specified herein, wherein (a) R$^8$ is hydrogen, C$_{1-4}$alkyl or arylC$_{1-4}$alkyl; or (b) R$^8$ is hydrogen or C$_{1-4}$alkyl; or (c) R$^8$ is hydrogen or methyl.

Other subgroups of the compounds of formula (I) are those compounds of formula (I), or any subgroup of compounds of formula (I) specified herein, wherein (a) $R^9$ and $R^{10}$ each independently are hydrogen; $C_{1-6}$alkyl; $C_{1-6}$alkylcarbonyl; $C_{1-6}$alkyloxycarbonyl; mono- or di($C_{1-6}$ alkyl)aminocarbonyl; —CH(=NR$^{11}$), wherein each of the aforementioned $C_{1-6}$alkyl groups may optionally be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, mono- and di($C_{1-4}$alkyl)amino, polyhalomethyl, polyhalomethyloxy;

(b) $R^9$ and $R^{10}$ each independently are hydrogen; $C_{1-6}$alkyl; $C_{1-6}$alkylcarbonyl or $C_{1-6}$alkyloxycarbonyl;

(c) $R^9$ and $R^{10}$ each independently are hydrogen or $C_{1-6}$alkyl;

(d) $R^9$ and $R^{10}$ are hydrogen.

Still other subgroups of the compounds of formula (I) are those compounds of formula (I), or any subgroup of compounds of formula (I) specified herein, wherein (a) $R^{13}$ and $R^{14}$ each independently are $C_{1-6}$alkyl optionally substituted with cyano, $C_{2-6}$alkenyl optionally substituted with cyano, $C_{2-6}$alkynyl optionally substituted with cyano;

(b) $R^{13}$ and $R^{14}$ each independently are hydrogen or $C_{1-6}$alkyl;

(c) $R^{13}$ and $R^{14}$ are hydrogen.

Still other subgroups of the compounds of formula (I) are those compounds of formula (I), or any subgroup of compounds of formula (I) specified herein, wherein $R^{15}$ is $C_{1-6}$alkyl optionally substituted with cyano.

Still other subgroups of the compounds of formula (I) are those compounds of formula (I), or any subgroup of compounds of formula (I) specified herein, wherein (a) $R^{16}$ is $C_{1-6}$alkyl optionally substituted with cyano or aminocarbonyl; or wherein (b) $R^{16}$ is $C_{1-6}$alkyl optionally substituted with cyano.

Still other subgroups of the compounds of formula (I) are those compounds of formula (I), or any subgroup of compounds of formula (I) specified herein, wherein (a) aryl is phenyl or phenyl substituted with one, two or three substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cyclo-alkyl, $C_{1-6}$alkyloxy, $C_{1-6}$alkyloxycarbonyl, $C_{1-6}$alkylthio, cyano, nitro, polyhalo-$C_{1-6}$alkyl, polyhalo$C_{1-6}$alkyloxy, aminocarbonyl, phenyl, thienyl and pyridyl;

(b) aryl is phenyl or phenyl substituted with one, two or three substituents each independently selected from halo, hydroxy, mercapto, $C_{1-6}$alkyl, hydroxy $C_{1-6}$alkyl, amino$C_{1-6}$alkyl, mono or di($C_{1-6}$alkyl)amino $C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, trifluoromethyl, trifluoromethoxy, aminocarbonyl, phenyl;

(c) aryl is phenyl or phenyl substituted with one, two or three substituents each independently selected from halo, hydroxy, $C_{1-6}$alkyl, hydroxy$C_{1-6}$alkyl, amino$C_{1-6}$alkyl, mono or di($C_{1-6}$alkyl)amino $C_{1-6}$alkyl, $C_{1-6}$alkylcarbonyl, $C_{1-6}$alkyloxy, $C_{1-6}$alkyloxycarbonyl, cyano, nitro, trifluoromethyl;

(d) aryl is phenyl or phenyl substituted with one, two or three substituents each independently selected from halo, hydroxy, $C_{1-6}$alkyl, $C_{1-6}$alkyloxy, cyano, nitro, trifluoromethyl.

One embodiment concerns a subgroup of compounds of formula (I) having the formula

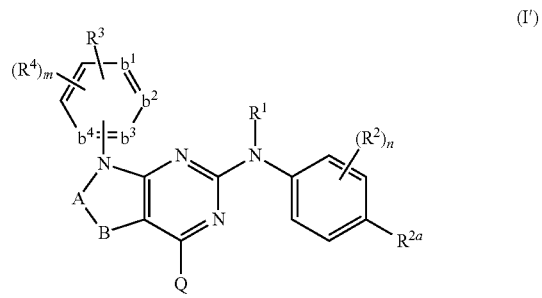

(I')

the N-oxides, the pharmaceutically acceptable addition salts, the quaternary amines or the stereochemically isomeric forms thereof, wherein -b$^1$=b$^2$-b$^3$=b$^4$-, R$^1$, each R$^2$, R$^{2a}$, R$^3$, each R$^4$, -A-B—, m, n and Q are as defined hereinabove in the general definition of the compounds of formula (I) or in the various subgroups thereof.

Yet another embodiment concerns a subgroup of compounds of formula (I) having the formula

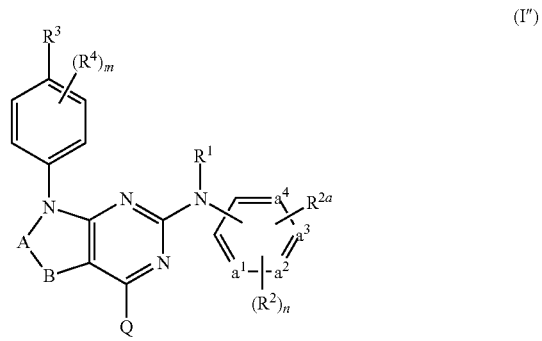

(I″)

the N-oxides, the pharmaceutically acceptable addition salts, the quaternary amines or the stereochemically isomeric forms thereof, wherein -a$^1$=a$^2$-a$^3$=a$^4$-, R$^1$, each R$^2$, R$^{2a}$, R$^3$, each R$^4$, -A-B—, m, n and Q are as defined hereinabove in the general definition of the compounds of formula (I) or in the various subgroups thereof.

Another embodiment concerns a subgroup of compounds of formula (I) having the formula

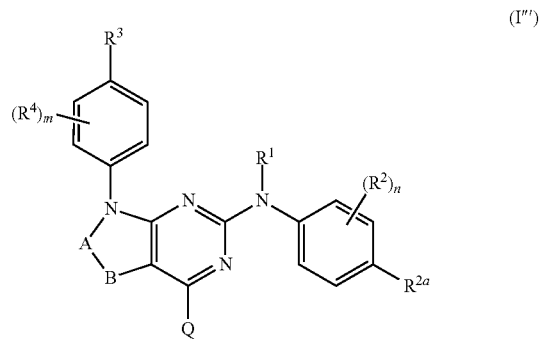

(I‴)

the N-oxides, the pharmaceutically acceptable addition salts, the quaternary amines or the stereochemically isomeric forms thereof, wherein $R^1$, each $R^2$, $R^{2a}$, $R^3$, each $R^4$, -A-B—, m, n and Q are as defined hereinabove in the general definition of the compounds of formula (I) or in the various subgroups thereof.

A further embodiment concerns a subgroup of compounds of formula (I) having the formula

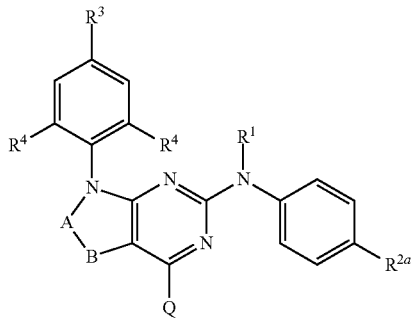

(I''')

the N-oxides, the pharmaceutically acceptable addition salts, the quaternary amines or the stereochemically isomeric forms thereof, wherein $R^1$, $R^{1a}$, $R^3$, each $R^4$, -A-B— and Q are as defined hereinabove in the general definition of the compounds of formula (I) or in the various subgroups thereof.

Also an interesting embodiment concerns a subgroup of compounds of formula (I) having the formula

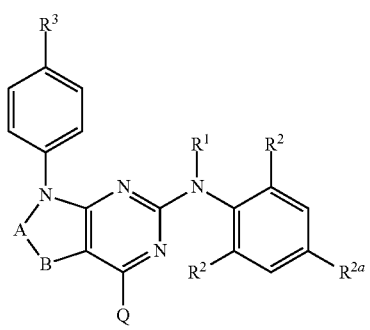

(I'''')

the N-oxides, the pharmaceutically acceptable addition salts, the quaternary amines or the stereochemically isomeric forms thereof, wherein $R^1$, $R^2$, $R^{2a}$, $R^3$, A-B— and Q are as defined hereinabove in the general definition of the compounds of formula (I) or in the various subgroups thereof.

Particular subgroups of compounds of formula (I), (I'), (I''), (I'''), (I'''') or (I''''') are those wherein -A-B— is a radical —$CR^5$=N— (c-1), wherein $R^{2a}$ has the meanings specified in (a)-(i), and $R^3$ has the meanings specified in (j)-(t), as follows:

(a) $R^{2a}$ is cyano; aminocarbonyl; amino; halo; $C_{1-6}$alkyloxy wherein $C_{1-6}$alkyl is substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one, two or three substituents each independently selected from halo, cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl and $R^7$; $C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl and $R^7$; $C_{2-6}$alkenyl substituted with one, two or three substituents each independently selected from halo, cyano, $NR^9R^{10}$, —C(=O)—$NR^9R^{10}$, —C(=O)—$C_{1-6}$alkyl and $R^7$; $C_{2-6}$alkynyl substituted with one, two or three substituents each independently selected from halo, cyano, $NR^9R^{10}$, —C(=O)—$NR^9R^{10}$, —C(=O)—$C_{1-6}$alkyl and $R^7$; —C(=N—O—$R^8$)—$C_{1-4}$alkyl; $R^7$ or —X—$R^7$;

(b) $R^{2a}$ is cyano; aminocarbonyl; amino; halo; $C_{1-6}$alkyloxy wherein $C_{1-6}$alkyl is substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one substituent selected from halo, cyano, $NR^9R^{10}$, —C(=O)—$NR^9R^{10}$, —C(=O)—$C_{1-6}$alkyl and $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one substituent selected from halo, cyano, $NR^9R^{10}$, —C(=O)—$NR^9R^{10}$, —C(=O)—$C_{1-6}$alkyl and $R^7$; $C_{2-6}$alkenyl substituted with one substituent selected from halo, cyano, $NR^9R^{10}$, —C(=O)—$NR^9R^{10}$, —C(=O)—$C_{1-6}$alkyl and $R^7$; $C_{2-6}$alkynyl substituted with one substituent selected from halo, cyano, $NR^9R^{10}$, —C(=O)—$NR^9R^{10}$, —C(=O)—$C_{1-6}$alkyl and $R^7$; —C(=N—O—$R^8$)—$C_{1-4}$alkyl; $R^7$ or —X—$R^7$;

(c) $R^{2a}$ is cyano; aminocarbonyl; amino; halo; $C_{1-6}$alkyloxy wherein $C_{1-6}$alkyl is substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one substituent selected from halo, cyano, —C(=O)—$NR^9R^{10}$; $C_{1-6}$alkyl substituted with hydroxy and a second substituent selected from halo, cyano, —C(=O)—$NR^9R^{10}$; $C_{1-6}$alkyloxy$C_{1-6}$alkyl optionally substituted with one substituent selected from halo, cyano, —C(=O)—$NR^9R^{10}$; $C_{2-6}$alkenyl substituted with one substituent selected from halo, cyano, —C(=O)—$NR^9R^{10}$; $C_{2-6}$alkynyl substituted with one substituent selected from halo, cyano, —C(=O)—$NR^9R^{10}$;

(d) $R^{2a}$ is halo, cyano, aminocarbonyl, $C_{1-6}$alkyl substituted with cyano or aminocarbonyl, $C_{2-6}$alkenyl optionally substituted with cyano or aminocarbonyl;

(e) $R^{2a}$ is halo, cyano, aminocarbonyl, $C_{1-6}$alkyl substituted with cyano or aminocarbonyl, or $C_{2-6}$alkenyl substituted with cyano or aminocarbonyl;

(f) $R^{2a}$ is cyano, aminocarbonyl, $C_{1-6}$alkyl substituted with cyano or $C_{2-6}$alkenyl substituted with cyano;

(g) $R^{2a}$ is cyano, aminocarbonyl, $C_{1-4}$alkyl substituted with cyano or $C_{2-4}$alkenyl substituted with cyano;

(h) $R^{2a}$ is cyano, $C_{1-4}$alkyl substituted with cyano or $C_{2-4}$alkenyl substituted with cyano; or (i) $R^{2a}$ is cyano;

(j) $R^3$ is cyano; aminocarbonyl; amino; halo; $C_{1-6}$alkyloxy wherein $C_{1-6}$alkyl is substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one, two or three substituents each independently selected from halo, cyano, $NR^9R^{10}$, —C(=O)—$NR^9R^{10}$, —C(=O)—$C_{1-6}$alkyl and $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl and $R^7$; $C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl and R$^7$; C$_{2-6}$alkenyl substituted with one, two or three substituents each independently selected from halo, cyano, NR$^9$R$^{10}$, —C(=O)—NR$^9$R$^{10}$, —C(=O)—C$_{1-6}$alkyl and R$^7$; C$_{2-6}$alkynyl substituted with one, two or three substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ and —X—R$^7$.

(k) R$^3$ is cyano; aminocarbonyl; amino; halo; C$_{1-6}$alkyloxy wherein C$_{1-6}$alkyl is substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one substituent selected from halo, cyano, NR$^9$R$^{10}$, —C(=O)—NR$^9$R$^{10}$, —C(=O)—C$_{1-6}$alkyl and R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl and R$^7$; C$_{1-6}$alkyloxyC$_{1-6}$alkyl optionally substituted with one substituent selected from halo, cyano, NR$^9$R$^{10}$, —C(=O)—NR$^9$R$^{10}$, —C(=O)—C$_{1-6}$alkyl and R$^7$; C$_{2-6}$alkenyl substituted with one substituent selected from halo, cyano, NR$^9$R$^{10}$, —C(=O)—NR$^9$R$^{10}$, —C(=O)—C$_{1-6}$alkyl and R$^7$; C$_{2-6}$alkynyl substituted with one substituent selected from halo, cyano, NR$^9$R$^{10}$, —C(=O)—NR$^9$R$^{10}$, —C(=O)—C$_{1-6}$alkyl and R$^7$; —C(=N—O—R$^8$)—C$_{1-4}$alkyl; R$^7$ or —X—R$^7$;

(l) R$^3$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one substituent selected from halo, cyano, —C(=O)—NR$^9$R$^{10}$; C$_{1-6}$alkyl substituted with hydroxy and a second substituent selected from halo, cyano, —C(=O)—NR$^9$R$^{10}$; C$_{1-6}$alkyloxyC$_{1-6}$alkyl optionally substituted with one substituent selected from halo, cyano, —C(=O)—NR$^9$R$^{10}$; C$_{2-6}$alkenyl substituted with one substituent selected from halo, cyano, —C(=O)—NR$^9$R$^{10}$; C$_{2-6}$alkynyl substituted with one substituent selected from halo, cyano, —C(=O)—NR$^9$R$^{10}$;

(m) R$^3$ is halo, cyano, aminocarbonyl, C$_{1-6}$alkyl optionally substituted with cyano or aminocarbonyl, C$_{2-6}$alkenyl optionally substituted with cyano or aminocarbonyl;

(n) R$^3$ is halo, cyano, aminocarbonyl, C$_{1-6}$alkyl substituted with cyano or aminocarbonyl, or C$_{2-6}$alkenyl substituted with cyano or aminocarbonyl;

(o) R$^3$ is cyano, C$_{1-4}$alkyl substituted with cyano or C$_{2-4}$alkenyl substituted with cyano;

(p) R$^3$ is C$_{1-4}$alkyl substituted with cyano or C$_{2-4}$alkenyl substituted with cyano;

(q) R$^3$ is C$_{2-4}$alkyl substituted with cyano or C$_{2-4}$alkenyl substituted with cyano;

(r) R$^3$ is C$_{2-4}$alkenyl substituted with cyano;

(s) R$^3$ is ethenyl substituted with cyano;

(t) R$^3$ is (E)-2-cyanoethenyl.

Particular subgroups of compounds of formula (I), (I'), (I''), (I'''), (I'''') or (I''''') are those wherein -A-B— is a radical —N=N— (c-2), or wherein -A-B— is a radical of formula —CH$_2$—CH$_2$— (c-3); and wherein (a) R$^3$ is C$_{1-6}$alkyl substituted with cyano or aminocarbonyl, or C$_{2-6}$alkenyl substituted with cyano or aminocarbonyl;

(b) R$^3$ is C$_{2-6}$alkyl substituted with cyano or aminocarbonyl, or C$_{2-6}$alkenyl substituted with cyano or aminocarbonyl;

(c) R$^3$ is C$_{2-4}$alkyl substituted with cyano or aminocarbonyl, or C$_{2-4}$alkenyl substituted with cyano or aminocarbonyl;

(d) R$^3$ is C$_{2-6}$alkyl substituted with cyano, or C$_{2-6}$alkenyl substituted with cyano;

(e) R$^3$ is C$_{2-4}$alkyl substituted with cyano, or C$_{2-4}$alkenyl substituted with cyano;

(f) R$^3$ is C$_{2-6}$alkenyl substituted with cyano or aminocarbonyl;

(g) R$^3$ is C$_{2-4}$alkenyl substituted with cyano or aminocarbonyl;

(h) R$^3$ is C$_{2-6}$alkenyl substituted with cyano;

(i) R$^3$ is C$_{2-6}$alkenyl substituted with cyano;

(j) R$^3$ is ethenyl substituted with cyano; or wherein (k) R$^3$ is (E)-2-cyanoethenyl.

Particular subgroups of compounds of formula (I), (I'), (I''), (I'''), (I'''') or (I''''') are those wherein -A-B— is a radical —N=N-(c-2), or wherein -A-B— is a radical of formula —CH$_2$—CH$_2$— (c-3); and wherein (a) R$^{2a}$ is cyano or aminocarbonyl; or wherein (b) R$^{2a}$ is cyano.

Particular subgroups of compounds of formula (I), (I'), (I''), (I'''), (I'''') or (I''''') are those wherein -A-B— is a radical —N=N-(c-2), or wherein -A-B— is a radical of formula —CH$_2$—CH$_2$— (c-3); and wherein (a) R$^3$ is C$_{1-6}$alkyl substituted with cyano or aminocarbonyl, or C$_{2-6}$alkenyl substituted with cyano or aminocarbonyl;

(b) R$^3$ is C$_{2-6}$alkyl substituted with cyano or aminocarbonyl, or C$_{2-6}$alkenyl substituted with cyano or aminocarbonyl;

(c) R$^3$ is C$_{2-4}$alkyl substituted with cyano or aminocarbonyl, or C$_{2-4}$alkenyl substituted with cyano or aminocarbonyl;

(d) R$^3$ is C$_{2-6}$alkyl substituted with cyano, or C$_{2-6}$alkenyl substituted with cyano;

(e) R$^3$ is C$_{2-4}$alkyl substituted with cyano, or C$_{2-4}$alkenyl substituted with cyano;

(f) R$^3$ is C$_{2-6}$alkenyl substituted with cyano or aminocarbonyl;

(g) R$^3$ is C$_{2-4}$alkenyl substituted with cyano or aminocarbonyl;

(h) R$^3$ is C$_{2-6}$alkenyl substituted with cyano;

(i) R$^3$ is C$_{2-6}$alkenyl substituted with cyano;

(j) R$^3$ is ethenyl substituted with cyano; or wherein (k) R$^3$ is (E)-2-cyanoethenyl;

and for each of the possibilities (a)-(k), R$^{2a}$ is cyano or aminocarbonyl; or R$^{2a}$ is cyano.

The compounds of formula (I) can be prepared by reacting an intermediate of formula (II-a) or (II-b) with an intermediate of formula (III-a) or (III-b). In this and the following reaction schemes each W independently represents a suitable leaving group, such as for example halogen, e.g. chloro, bromo, iodo, an acetate group, a nitrobenzoate group, an azide group, an arylsulfonyl group, e.g. tosylate, brosylate, mesylate, nosylate, triflate, and the like. Of particular interest are halo groups, in particular chloro or bromo.

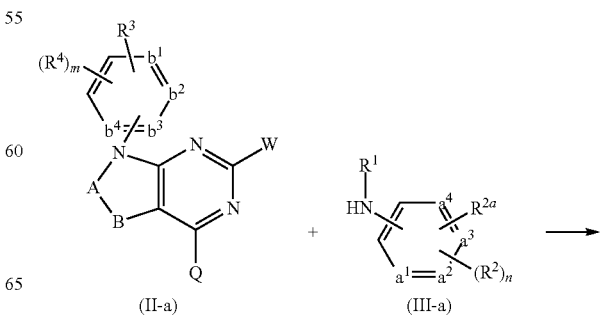

-continued

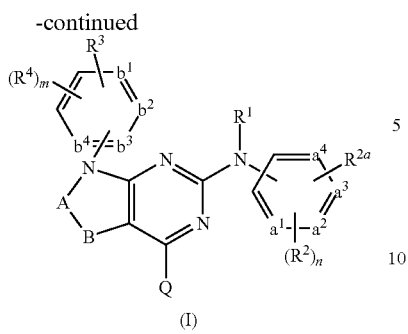

(I)

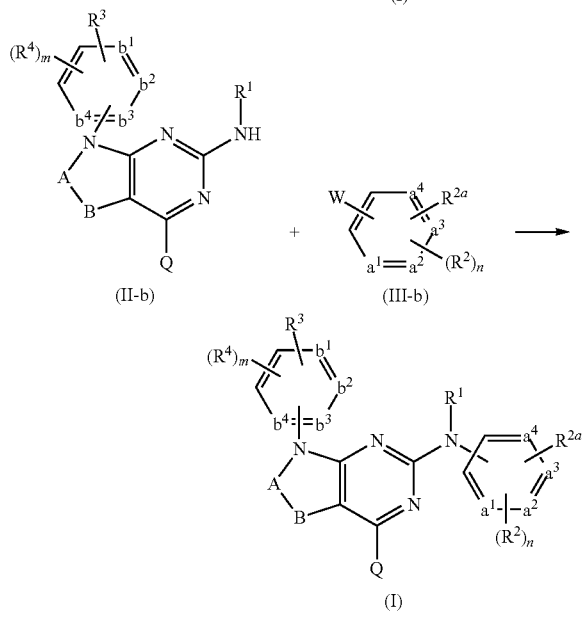

The reaction of the pyrimidine derivative (II-a) respectively (II-b) with the amine (III-a) respectively the intermediate (III-b) is typically conducted in a suitable solvent. Suitable solvents are for example an alcohol, such as for example ethanol, 2-propanol; a dipolar aprotic solvent such as acetonitrile, N,N-dimethylformamide; N,N-dimethylacetamide, 1-methyl-2-pyrrolidinone; an ether such as tetrahydrofuran, 1,4-dioxane, propylene glycol monomethylether. These reactions can be conducted under neutral conditions or, which is preferred, at acidic conditions, usually at elevated temperatures and under stirring. The acid conditions may be obtained by adding amounts of a suitable acid e.g. camphor sulfonic acid or by using acid solvents, e.g. hydrochloric acid or in an alkanol such as 1- or 2-propanol, or an ether such as tetrahydrofuran.

The compounds of formula (I) can also be prepared by reacting the bicyclic derivative (IV) with (V) as outlined in the following scheme.

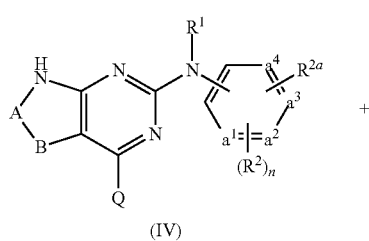

-continued

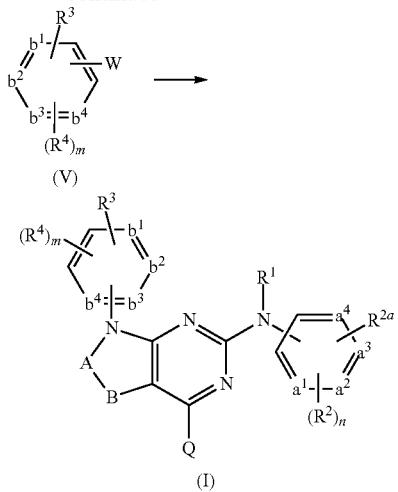

In this reaction scheme W represents an appropriate leaving group as specified above. The reaction is conducted using similar reaction conditions as outlined above for the reactions of (II-a) with (III-a) and (II-b) with (III-b).

The compounds of formula (I-a) which are compounds of formula (I) wherein -A-B— is —CH$_2$—CH$_2$— can be prepared by reacting a pyrimidine derivative (VI) wherein each W is a leaving group as specified above and preferably is chloro or bromo, with an aromatic amine of formula (VII).

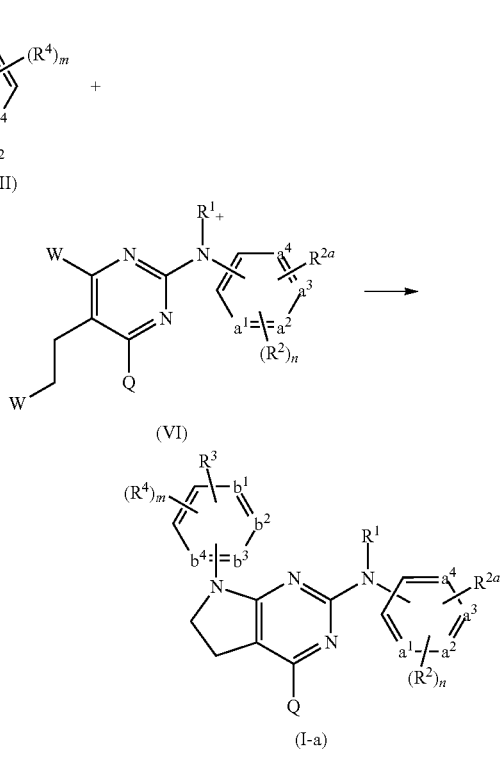

The compounds of formula (I-a) can be converted to the corresponding compounds (I-b) which are compounds of formula (I) wherein -A-B— is —CH=CH—, by an elimination reaction, in particular by eliminating hydrogen from a corresponding saturated analog (I-a), using an appropriate dehydrogenating reagent such as, e.g., 2,3-dichloro-5,6-dicyano-1,4-benzoquinone (DDQ).

This reaction may be conducted in a suitable solvent such as an alcohol, e.g. methanol, ethanol, or an ether, e.g. THF or dioxane, or mixtures thereof.

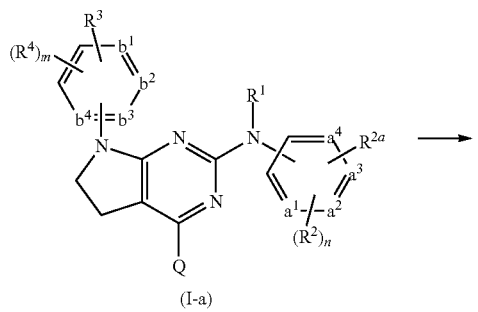

(I-a)

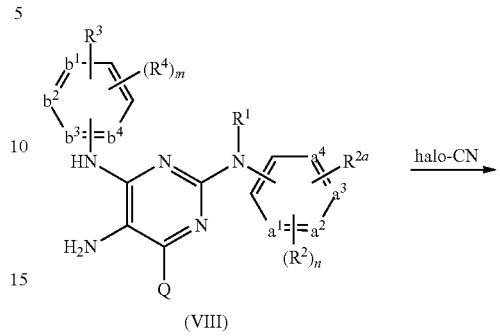

(VIII)

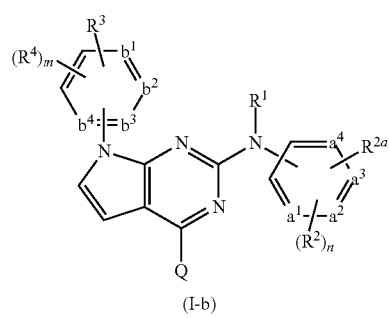

(I-b)

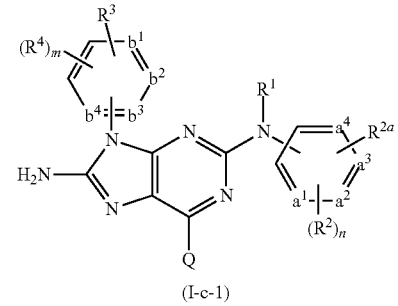

(I-c-1)

The compounds of formula (I-c) which are compounds of formula (I) wherein -A-B— is —CR⁵=N— can be prepared by reacting an aminopyrimidine (VIII) with an orthoformate R⁵C(OEt)₃ or with an aldehyde R⁵CH=O in the presence of a mild oxidant such as nitrobenzene.

The compounds of formula (I-c-1) can be mono- or bis-alkylated to the corresponding compounds wherein R⁵ is mono- or di(C₁₋₄alkyl)amino using a reagent C₁₋₄alkyl-W as alkylating agent.

The compounds of formula (I-d), which are compounds of formula (I) wherein -A-B— is —N=N—, can be prepared by reacting an aminopyrimidine (VIII) with a diazo-forming reagent such as a nitrite, in particular an alkali metal nitrite, e.g. sodium or potassium nitrite in the presence of acetic acid.

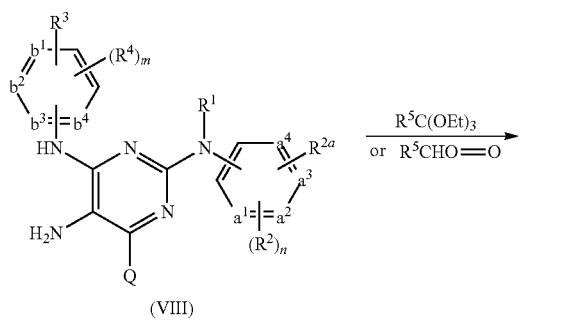

(VIII)

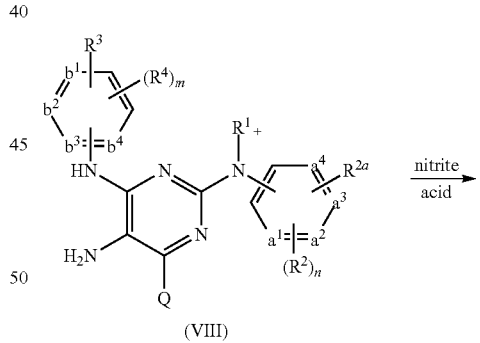

(VIII)

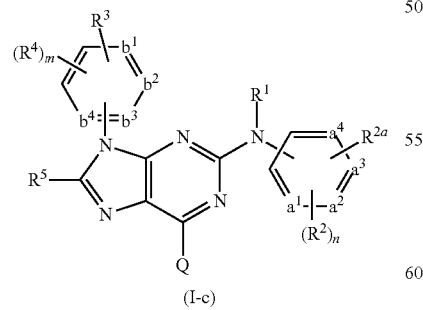

(I-c)

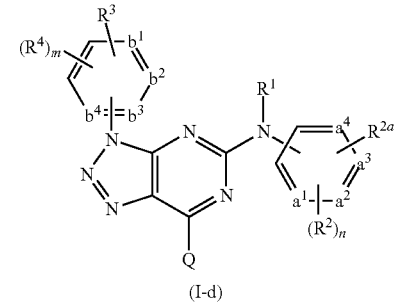

(I-d)

The compounds of formula (I-c-1) which are compounds of formula (I) wherein -A-B— is —CR⁵=N— wherein R⁵ is amino can be prepared by reacting an aminopyrimidine (VIII) with a cyanogen halide, in particular with cyanogen bromide.

The compounds of formula (I-e) or (I-f) which are compounds of formula (I) wherein -A-B— is —CS—NH— or, respectively, —CO—NH—, can be prepared by reacting an aminopyrimidine (VIII) with a thiophosgene derivative $(W^1)_2C=S$, yielding compounds (I-e) or with a phosgene derivative $(W^1)_2C=O$, yielding compounds (I-f). In these reaction schemes, each $W^1$ independently represents a leaving group such as the groups W specified above, preferably $W^1$ is halo, in particular chloro.

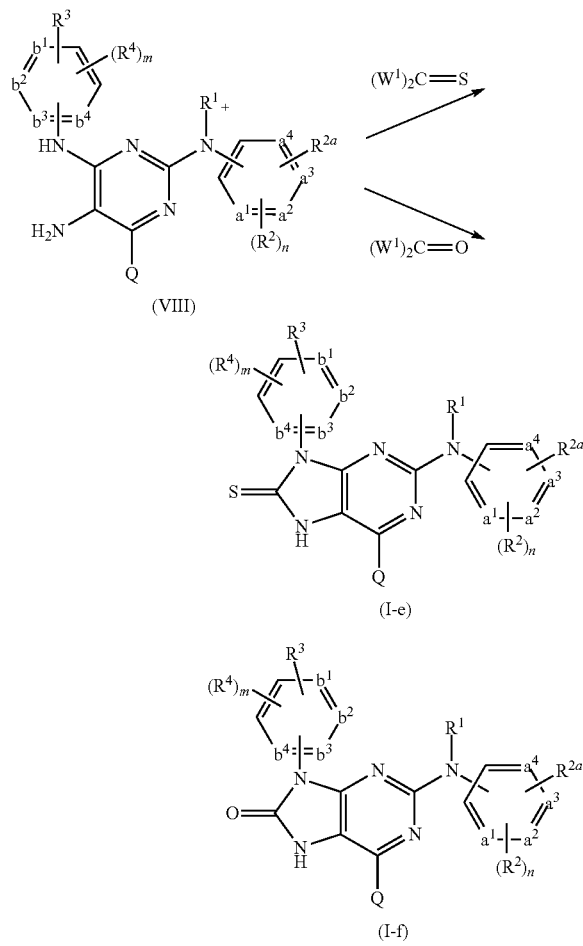

In any of the above or the following reaction schemes each of the radicals $R^2$, $R^{2a}$, $R^3$ or $R^4$ may be as defined above or may also be a precursor group, which is converted to the desired $R^2$, $R^{2a}$, $R^3$ or $R^4$ group. For example, the compounds of formula (I) wherein $R^3$ is $C_{2-6}$alkenyl substituted with one, two or three substituents each independently selected from halo, cyano, $NR^9R^{10}$, —C(=O)—$NR^9R^{10}$, —C(=O)—$C_{1-6}$alkyl or $R^7$, may be prepared starting from the analogs of these compounds wherein $R^3$ is an ester group such as a $C_{1-6}$alkyloxycarbonyl group, which is reduced to a hydroxymethylene group, e.g. with a complex metal hydride such as lithium aluminum hydride, which subsequently is oxidized to an aldehyde group using a mild oxidant (for example $MnO_2$). The aldehyde group is then converted into an alkenyl or substituted alkenyl group using a Wittig reaction or a Wittig-Horner reaction. In the former instance a Wittig type reagent, such as a triphenyl-phosphoniumylide is used. The Wittig conversion is conducted in a suitable reaction-inert solvent such as an ether, starting from triphenylphosphine and e.g. a halo acetonitrile (e.g. chloroacetonitrile) or a halo acetic acid ester of formula $R^x$—CH(Halo)-$COOR^y$, wherein $R^x$ and $R^y$ independently are $C_{1-6}$alkyl, $C_{1-4}$alkyl or $C_{1-2}$alkyl groups. The Wittig-Horner reaction is performed using a phosphonate, such as e.g. a reagent of formula di($C_{1-6}$alkyl-oxy)-P(=O)—CH($R^x$)—$COOR^y$ or di($C_{1-6}$alkyloxy)-P(=O)—CH($R^x$)—CN in the presence of a base, preferably a strong base, e.g. an alkali metal alkoxide such as sodium or potassium methoxide, ethoxide, t.butyloxide, in an ether, e.g THF or dioxane, an aprotic organic solvent, e.g. DMF, DMA, HMPT, DMSO and the like. A similar reaction sequence may be followed for those compounds of formula (I) wherein $R^2$, $R^{2a}$ or $R^4$ is a substituted $C_{2-6}$alkenyl group as specified above.

Any of the conversions of the intermediates as described hereinafter can also be applied on analogs of the compounds of formula (I) wherein $R^2$, $R^{2a}$, $R^3$ or $R^4$ is a precursor group. For example, the reaction of (III-b) or (V-b) with (XIII) to yield (III-c) or (V-c), of (III-f) to (III-c), of (V-f) to (V-c), of (III-b) to (III-f) etc., all these reactions being described hereinafter in more detail, may also be applied to analogs of the starting materials wherein the —$NHR^1$ group is a group

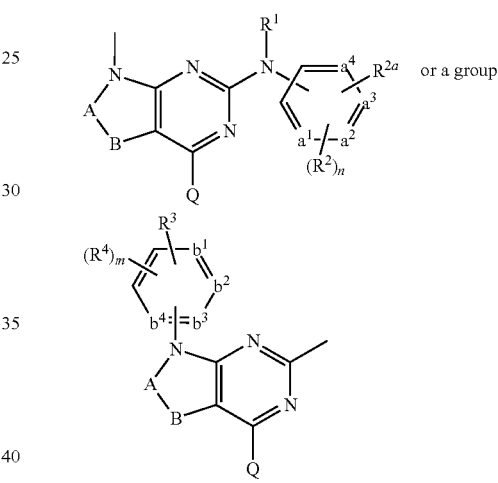

The compounds of formula (I) may further be prepared by converting compounds of formula (I) into each other according to art-known group transformation reactions. The compounds of formula (I) may be converted to the corresponding N-oxide forms following art-known procedures for converting a tertiary nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^2$, $R^{2a}$, $R^3$ or $R^4$ is $C_{2-6}$alkenyl substituted with aminocarbonyl, can be converted into a compound of formula (I) wherein $R^2$, $R^{2a}$, $R^3$ or $R^4$ is $C_{2-6}$alkenyl substituted with cyano by reaction with $POCl_3$.

Compounds of formula (I) wherein m is zero, can be converted into a compound of formula (I) wherein m is other than zero and R⁴ represents halo, by reaction with a suitable halo-introducing agent, such as for example N-chlorosuccinimide or N-bromo-succinimide, or a combination thereof, in the presence of a suitable solvent, such as for example acetic acid.

Compounds of formula (I) wherein R³ represents halo, may be converted into a compound of formula (I) wherein R³ represents $C_{2-6}$alkenyl substituted with one or more substituents each independently selected from halo, cyano, $NR^9R^{10}$, —C(=O)—$NR^9R^{10}$, —C(=O)—$C_{1-6}$alkyl or R⁷, by reaction with the corresponding $C_{2-6}$alkene substituted with one or more substituents each independently selected from halo, cyano, $NR^9R^{10}$, —C(=O)—$NR^9R^{10}$, —C(=O)—$C_{1-6}$alkyl or R⁷ in the presence of a suitable base, such as for example N,N-diethylethanamine, a suitable catalyst, such as for example palladium acetate in the presence of triphenylphosphine, and a suitable solvent, such as for example N,N-dimethylformamide.

Compounds of formula (I) wherein $R^{2a}$ represents halo, may be converted into a compound of formula (I) wherein $R^{2a}$ represents $C_{2-6}$alkenyl substituted with one or more substituents each independently selected from halo, cyano, $NR^9R^{10}$, —C(=O)—$NR^9R^{10}$, —C(=O)—$C_{1-6}$alkyl or R⁷, by reaction with the corresponding $C_{2-6}$alkene substituted with one or more substituents each independently selected from halo, cyano, $NR^9R^{10}$, —C(=O)—$NR^9R^{10}$, —C(=O)—$C_{1-6}$alkyl or R⁷ in the presence of a suitable base, such as for example N,N-diethyl-ethanamine, a suitable catalyst, such as for example palladium acetate in the presence of triphenylphosphine, and a suitable solvent, such as for example N,N-dimethylformamide.

Compounds of formula (I) wherein R¹ represents $C_{1-6}$alkyloxycarbonyl, can be converted into a compound of formula (I) wherein R¹ represents hydrogen, by reaction with a suitable base, such as for example sodium hydroxide or methoxide. Where R¹ is t.butyloxycarbonyl, the corresponding compounds wherein R¹ is hydrogen can be made by treatment with trifluoroacetic acid.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be available commercially or may be prepared according to art-known procedures.

Intermediates of formula (II-a) can be prepared as outlined in the following reaction scheme. In this scheme W represents a suitable leaving group, such as the W groups specified above, or a precursor of a leaving group that can conveniently be converted into a leaving group, e.g. a hydroxy function or a protected hydroxy function, by reaction with a halogenating agent. B¹ represents a precursor of B such as an amino group or a group —CH₂—CH₂—W. The -A-B-linking agent can be any of the agents mentioned above in the preparation of compounds (I-a), (I-c), (I-d), (I-e) and (I-f). The same or similar reaction conditions as described for the preparation of the latter compounds can also be used in the preparation of (II-a).

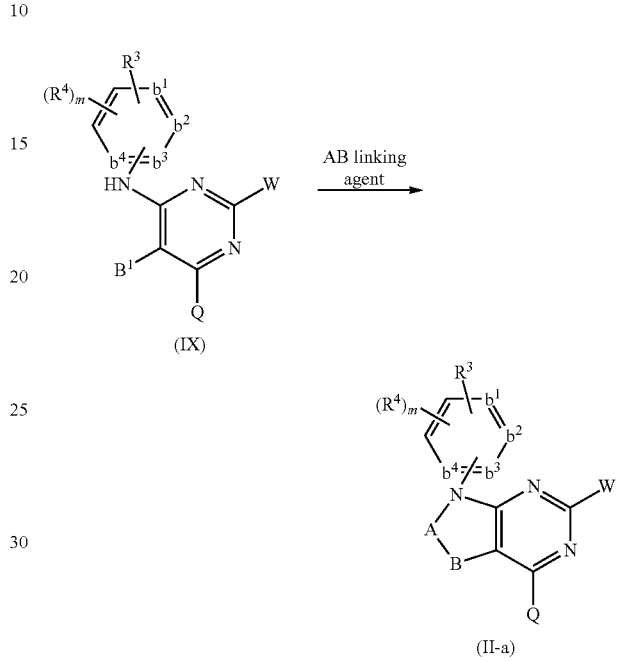

In a similar manner, intermediates (II-b) can be prepared starting from a pyrimidine (X) as outlined in the following scheme:

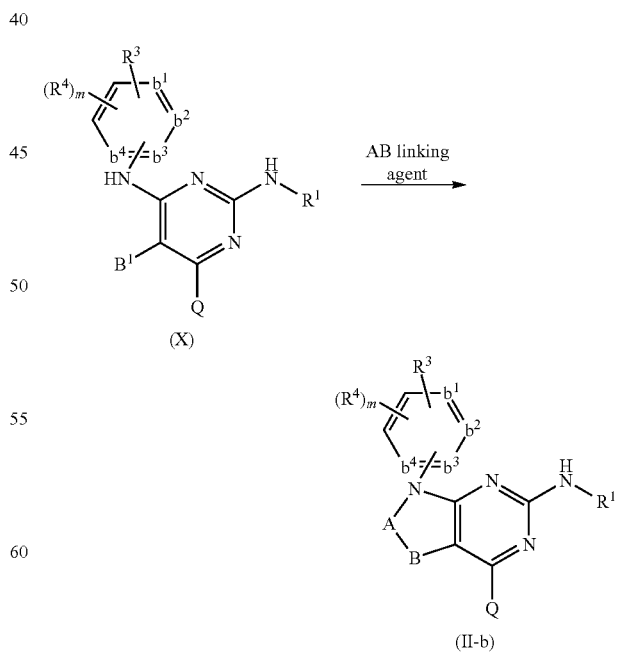

In the above reaction the amino group may or may not be protected by a suitable protective group, e.g., an acetyl, trifluoroacetyl, benzyl, butyloxycarbonyl, benzyloxycarbonyl and the like N-protecting groups.

Intermediates of formula (III-a) wherein $R^1$ is hydrogen, said intermediates being represented by formula (III-a'), or intermediates of formula (VII), can be prepared by reacting intermediates of formula (XI) or (XII) with a suitable reducing agent, such as Fe, in the presence of $NH_4Cl$ and a suitable solvent, such as for example tetrahydrofuran, $H_2O$ and an alcohol, e.g. methanol and the like. The intermediates of formula (III-a') can be converted to intermediates of formula (III-a) wherein $R^1$ is other than hydrogen, by an N-alkylation reaction with a reagent $R^1$—W, wherein W is as specified above.

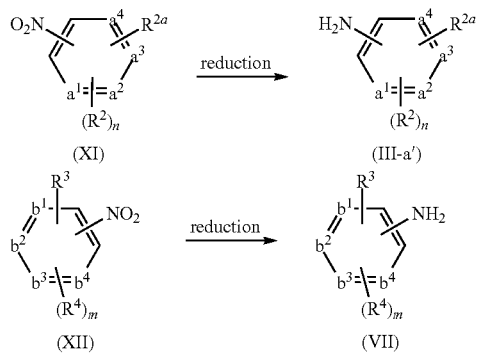

Intermediates of formula (III-b) or (V) are either commercially available or can be prepared in a straightforward manner, e.g. by converting corresponding intermediates having a hydroxy function into a group W, e.g. by reaction with a halogenating agent (e.g. $POCl_3$, $SOCl_2$, $PCl_3$ and the like).

Intermediates of formula (III-a) wherein $R^{2a}$ represents $C_{2-6}$alkyl substituted with cyano and $R^1$ is hydrogen, said intermediates being represented by formula (III-a-1), can be prepared by reacting an intermediate of formula (XI-a) with Pd/C in the presence of a suitable solvent, such as for example an alcohol, e.g. ethanol and the like. Similarly, intermediates of formula (XII-a) may be converted to intermediates of formula (VII-a), which are intermediates of formula (VII) wherein $R^{2a}$ represents $C_{2-6}$alkyl substituted with cyano.

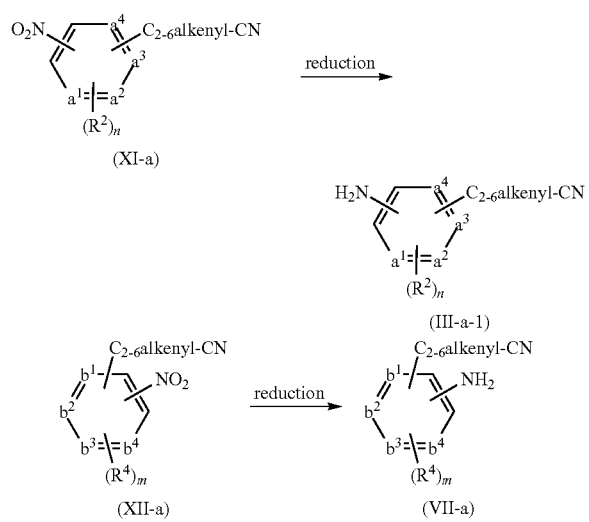

Intermediates of formula (III-a) or (VII) wherein $R^{2a}$ or $R^3$ is halo, said intermediates being represented by formula (III-a-2) and (VII-b), may be converted into intermediates of formula (III-a-3) and (VII-c) respectively, wherein $R^{2a}$ respectively $R^3$ is $C_{2-6}$alkenyl substituted with C(=O)$NR^9R^{10}$, by reacting the starting intermediates with an intermediate of formula (XIII) in the presence of $Pd(OAc)_2$, P(o-Tol)$_3$, a suitable base, e.g. N,N-diethylethanamine, and a suitable solvent, such as for example $CH_3CN$.

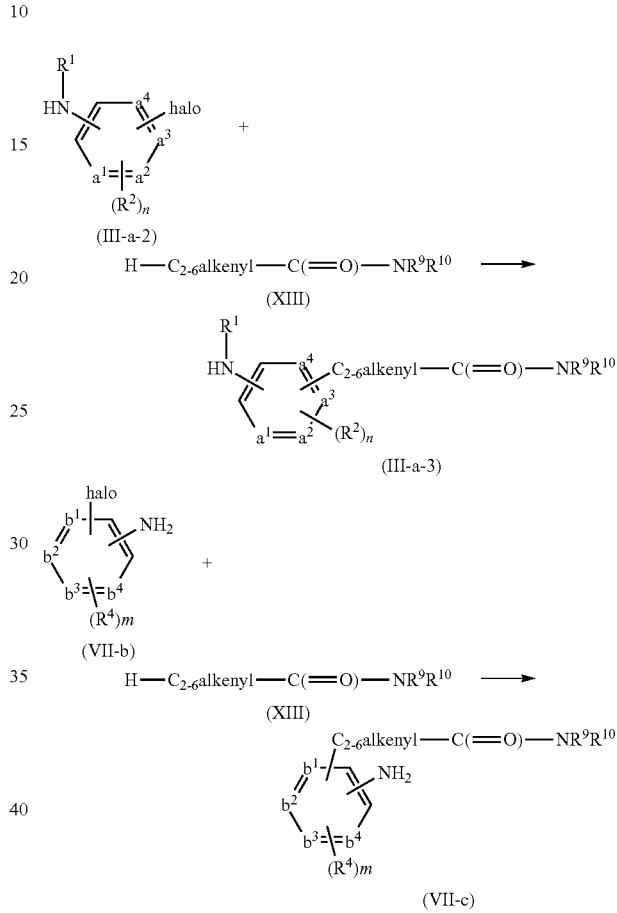

Intermediates of formula (III-a-3) and (VII-c) can also be prepared by reacting intermediates of formula (III-a-4) or (VII-d) with H—$NR^9R^{10}$ in the presence of oxalyl chloride and in the presence of a suitable solvent, such as for example N,N-dimethyl-formamide, $CH_2Cl_2$ and tetrahydrofuran.

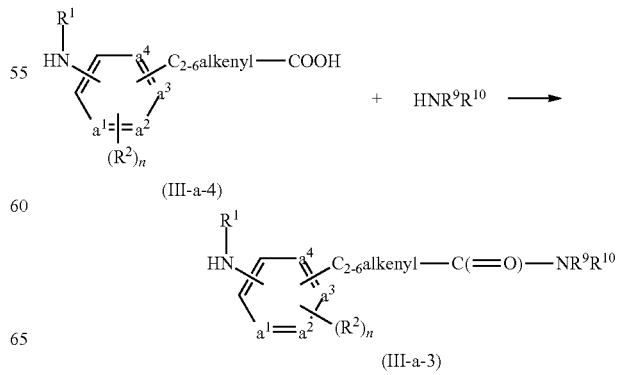

(VII-d)

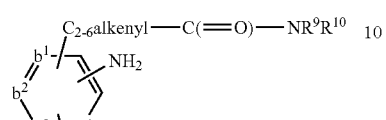
(VII-c)

Intermediates of formula (III-a-4) and (VII-d) can be prepared by reacting intermediates of formula (III-a-2) and (VII-b), with H—$C_{2-6}$alkenyl-C(=O)—OH in the presence of Pd(OAc)$_2$, P(o-Tol)$_3$, a suitable base, such as for example N,N-diethylethanamine, and a suitable solvent, such as for example CH$_3$—CN.

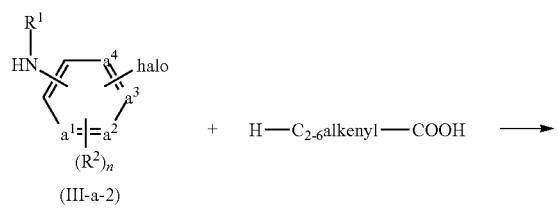
(III-a-2)

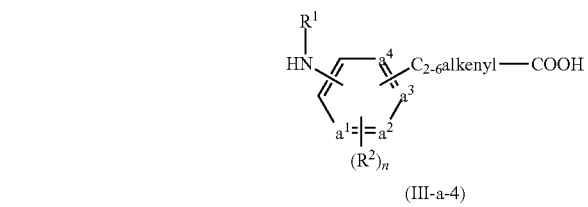
(III-a-4)

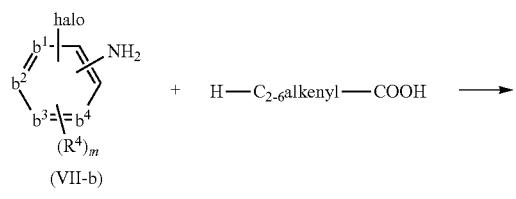
(VII-b)

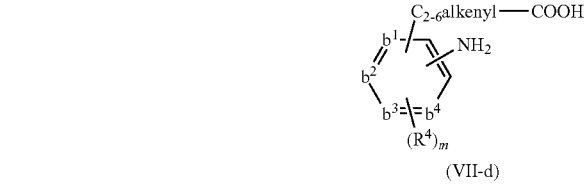
(VII-d)

Intermediates of formula (III-a-2) and (VII-b) may also be converted into intermediates of formula (III-a) or (VII) wherein $R^{2a}$ respectively $R^3$ is $C_{2-6}$alkenyl substituted with CN, said intermediates being represented by formula (III-a-5) and (VII-e) by reaction with H—$C_{2-6}$alkenyl-CN in the presence of Pd(OAc)$_2$, P(o-Tol)$_3$, a suitable base, such as for example N,N-diethylethanamine, and a suitable solvent, such as for example CH$_3$—CN.

(III-a-2)

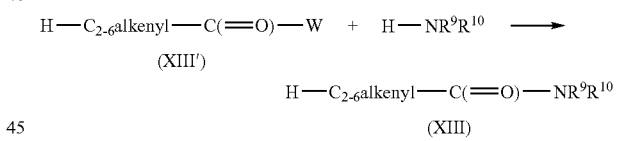
(III-a-5)

(VII-b) + H—$C_{2-6}$alkenyl—CN ⟶

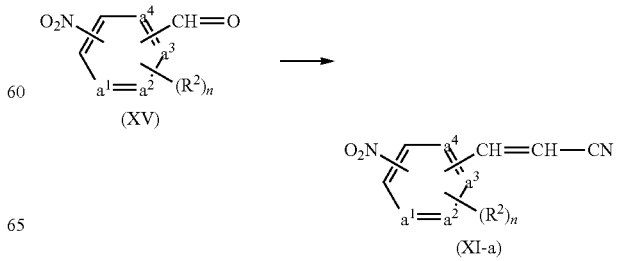
(VII-e)

Intermediates of formula (XIII) can be prepared by reacting an intermediate of formula (XIII') wherein W represents a suitable leaving group, such as defined above and in particular is halogen, e.g. chloro, with H—NR$^9$R$^{10}$ in the presence of a suitable solvent, such as for example diethylether and tetrahydrofuran.

H—$C_{2-6}$alkenyl—C(=O)—W + H—NR$^9$R$^{10}$ ⟶
(XIII')

H—$C_{2-6}$alkenyl—C(=O)—NR$^9$R$^{10}$
(XIII)

Intermediates of formula (XI) or (XII) wherein $R^{2a}$ respectively $R^3$ represents cyanovinyl, said intermediates being represented by formula (XI-a) and (XII-a), can be prepared by reacting an intermediate of formula (XV) respectively (XVI) with diethylcyanomethyl-phosphonate in the presence of a suitable base, such as for example NaOCH$_3$, and a suitable solvent, such as for example tetrahydrofuran.

O$_2$N—...—CH=O
(XV)

O$_2$N—...—CH=CH—CN
(XI-a)

-continued

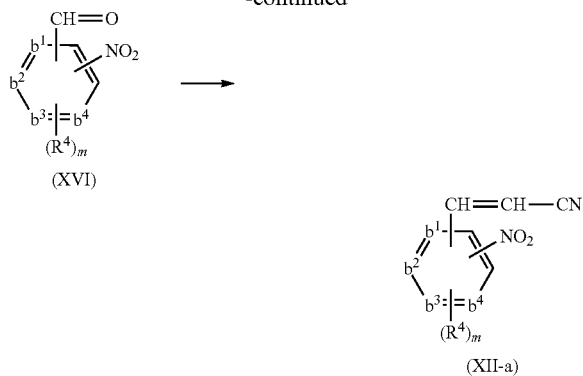

Intermediates of formula (XI) or (XII) wherein $R^{2a}$ respectively $R^3$ represents —C(CH₃)=CH—CN, said intermediates being represented by formula (XI-b) and (XII-b), can be prepared by reacting an intermediate of formula (XV') respectively (XVI') with diethylcyanomethylphosphonate in the presence of a suitable base, such as for example NaOCH₃, and a suitable solvent, such as for example tetrahydrofuran.

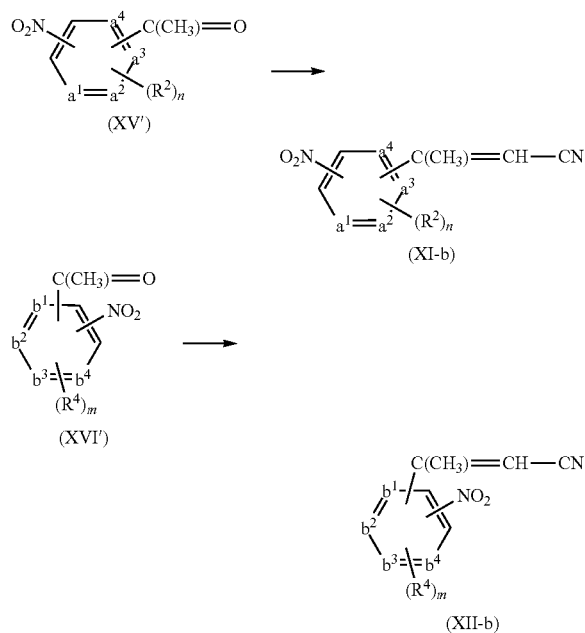

Intermediates of formula (XV) and (XVI) can be prepared by reacting an intermediate of formula (XVII) respectively (XVIII) with a suitable oxidizing agent, such as for example MnO₂, in the presence of a suitable solvent, such as for example a ketone, e.g. acetone, an ether, e.g. THF or dioxane, a halogenated hydrocarbon, e.g. dichloromethane or chloroform.

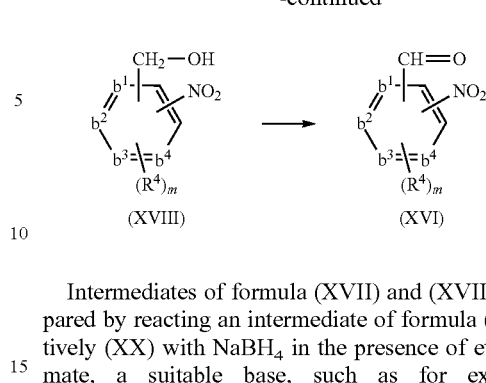

Intermediates of formula (XVII) and (XVIII) can be prepared by reacting an intermediate of formula (XIX) respectively (XX) with NaBH₄ in the presence of ethylchloroformate, a suitable base, such as for example N,N-diethylethanamine, and a suitable solvent, such as for example tetrahydrofuran.

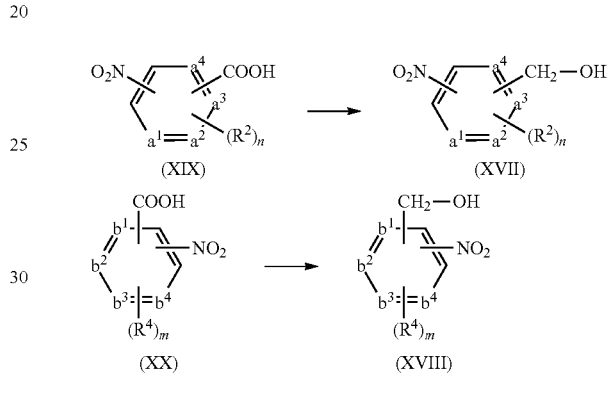

Intermediates of formula (XI) and (XII) wherein $R^{2a}$ respectively $R^3$ represent hydroxy, said intermediates being represented by formula (XI-c) respectively (XII-c), can be converted into an intermediate of formula (XI) respectively (XII) wherein $R^{2a}$ respectively $R^3$ represent $C_{1-6}$alkyloxy wherein the $C_{1-6}$alkyl may optionally be substituted with cyano, said $R^{2a}$ respectively $R^3$ being represented by P and said intermediates being represented by formula (XI-d) respectively (XII-d), by reaction with an intermediate of formula (XXI) wherein W represents a suitable leaving group, such as the leaving groups mentioned above, and in particular is halogen, e.g. chloro and the like, optionally in the presence of a catalyst such as an alkali metal iodide, e.g. NaI or KI, and further optionally in the presence of a suitable base, such as for example an alkali metal carbonate, e.g. K₂CO₃, and a suitable solvent, such as for example a ketone, e.g. acetone, an ether, e.g. THF, dioxane, a halogenated hydrocarbon, e.g. chloroform, dichloromethane.

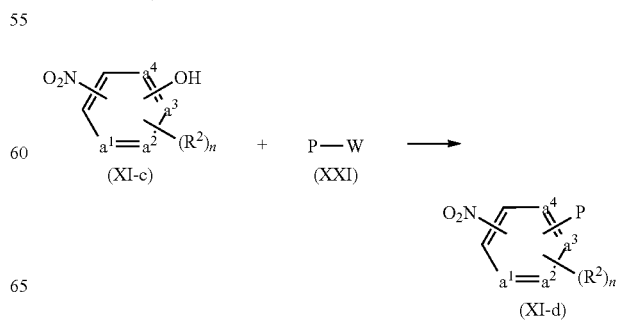

-continued

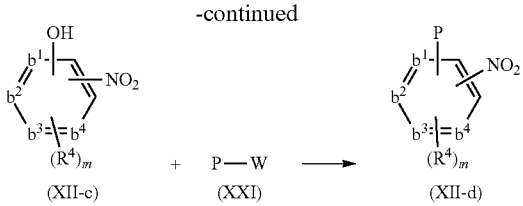

Intermediates of formula (XI) and (XII) can be prepared by reacting an intermediate of formula (XXII) respectively (XXIII) with $NaNO_3$ in the presence of $CH_3SO_3H$.

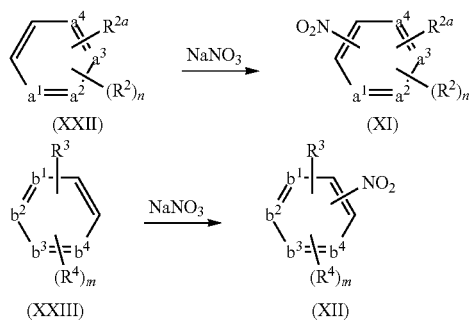

Intermediates of formula (IV) can be prepared by reacting an intermediate of formula (XXIV) wherein W is as specified above, with (III-a):

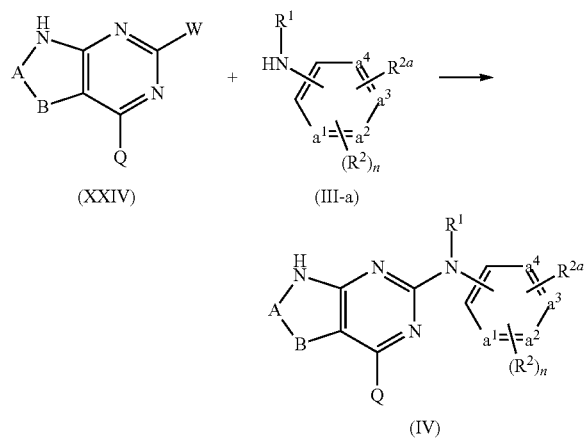

The intermediates (XXIV) are either commercially available or can be prepared by using an -A-B-linking agent as described above in the reactions of (IX) to (II-a) and (X) to (II-b).

The compounds of formula (I) show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclo-dextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in case the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions, which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
 a) mixing a compound of formula (I) and an appropriate water-soluble polymer,
 b) optionally blending additives with the thus obtained mixture,
 c) heating and compounding the thus obtained blend until one obtains a homogenous melt,
 d) forcing the thus obtained melt through one or more nozzles; and
 e) cooling the melt until it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 µm, preferably less than 400 µm and most preferably less than 125 µm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gum arabic, guar gum and xanthan gum, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water-soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins, which can be used to prepare the particles described above include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl-$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as antivirals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), D-D4FC (Reverset™), alovudine (MTV-310), amdoxovir (DAPD), elvucitabine (ACH-126,443), and the like; non-nucleoside reverse transcriptase inhibitors (NNRTIs) such as delarvidine (DLV), efavirenz (EFV), nevirapine (NVP), capravirine (CPV), calanolide A, TMC120, etravirine (TMC125), TMC278, BMS-561390, DPC-083 and the like; nucleotide reverse transcriptase inhibitors (NtRTIs), e.g. tenofovir (TDF) and tenofovir disoproxil fumarate, and the like; compounds of the TIBO (tetrahydroimidazo[4,5,1-jk] [1,4]-benzodiazepine-2(1H)-one and thione)-type e.g. (S)-8-chloro-4,5,6,7-tetrahydro-5-methyl-6-(3-methyl-2-butenyl) imidazo-[4,5,1-jk][1,4]-benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335; REV inhibitors; protease inhibitors e.g. ritonavir (RTV), saquinavir (SQV), lopinavir (ABT-378 or LPV), indinavir (IDV), amprenavir (VX-478), TMC-126, BMS-232632, VX-175, DMP-323, DMP-450 (Mozenavir), nelfinavir (AG-1343), atazanavir (BMS 232, 632), palinavir, TMC-114, RO033-4649, fosamprenavir (GW433908 or VX-175), P-1946, BMS 186,318, SC-55389a, L-756,423, tipranavir (PNU-140690), BILA 1096 BS, U-140690, and the like; entry inhibitors which comprise fusion inhibitors (e.g. T-20, T-1249), attachment inhibitors and co-receptor inhibitors; the latter comprise the CCR5 antagonists and CXR4 antagonists (e.g. AMD-3100); examples of entry inhibitors are enfuvirtide (ENF), GSK-873,140, PRO-542, SCH-417,690, TNX-355, maraviroc (UK-427,857); a maturation inhibitor for example is PA-457 (Panacos Pharmaceuticals); inhibitors of the viral integrase; ribonucleotide reductase inhibitors (cellular inhibitors), e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

The present invention is explained in greater detail in the following non-limiting examples.

EXAMPLES

Example 1

Synthesis of Intermediates B, C and D

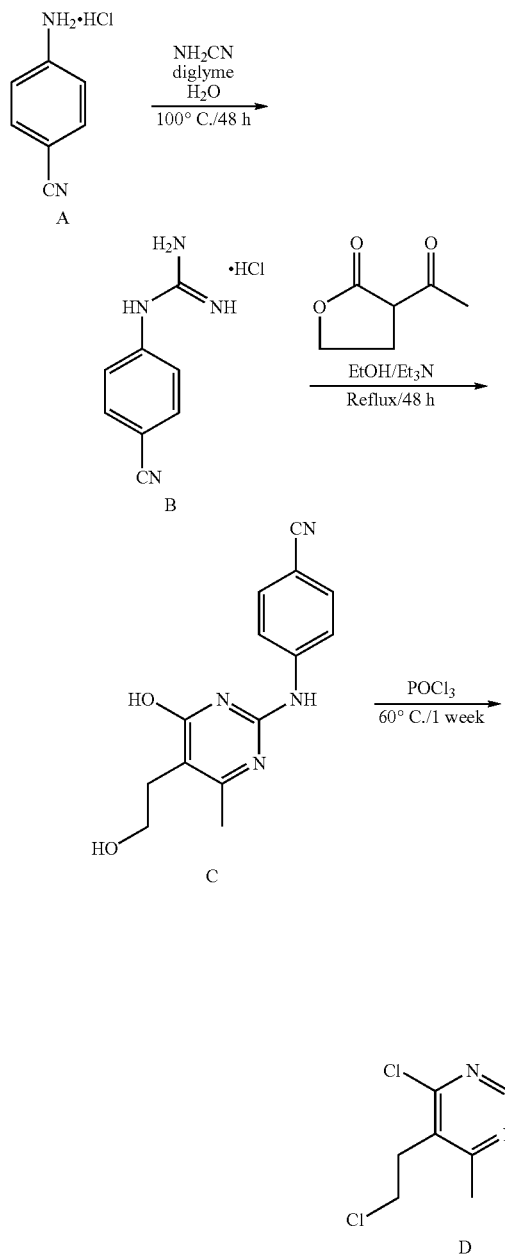

Preparation of Intermediate B

A mixture of A (0.420 mol) in 2-methoxyethylether (diglyme, 250 ml) was stirred at 100° C. for 30 minutes. Then a mixture of cyanamide (0.630 mol) in water (30 ml) was added portion wise during 45 minutes. After stirring 24 h at 100° C., cyanamide (0.210 mol) was added. The mixture was stirred again at 100° C. for 48 h. The mixture was evaporated until dryness and the residue was crystallized from acetone. Yield: 70.5 g of intermediate B (85%, melting point: 225° C.).

Preparation of Intermediate C

A mixture of B (0.356 mol) and 2-acetylbutyrolactone (1.068 mol) in ethanol (200 ml) and trietylamine (75 ml) was stirred at reflux for 48 h. The mixture was cooled and the precipitate was filtrated, then washed with ethanol and dried. Yield: 71 g of C (74%, melting point >250° C.).

Preparation of Intermediate D

A mixture of C (0.189 mol) and phosphorus oxychloride (200 ml) was stirred at 60° C. for 1 week. After cooling phosphorus oxychloride was evaporated. Water and $K_2CO_3$ 10% was added and the mixture was extracted with $CH_2Cl_2$. The organic layer was dried over magnesium sulfate, filtered and the solvent evaporated. Yield: 45 g of D (78%, melting point: 168° C.).

Example 2

Preparation of Intermediate E9
(4-bromo-2-chloro-6-fluoroaniline)

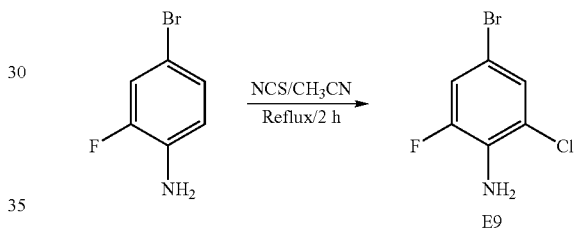

N-chlorosuccinimide (0.199 mol) was added portionwise to a mixture of 4-bromo-2-fluoroaniline (0.158 mol) in acetonitrile (50 ml). The mixture was stirred at reflux for 2 hours, cooled and poured in a mixture of water and $K_2CO_3$ 10%. The mixture was extracted with $CH_2Cl_2$. The organic layer was dried over magnesium sulfate, filtered and the solvent evaporated. The residue was purified by column chromatography over silica gel (eluent: cyclohexane/ethyl acetate 80/20; 35-70 μm). The pure fractions were collected and the solvent evaporated. Yield: 31.6 g of 4-bromo-2-chloro-6-fluoroaniline, intermediate E9 (89%, melting point: <50° C.). Intermediate E9 was used to prepare intermediate F9 (see Table 1).

Example 3

Preparation of Intermediates F3, F4, F6

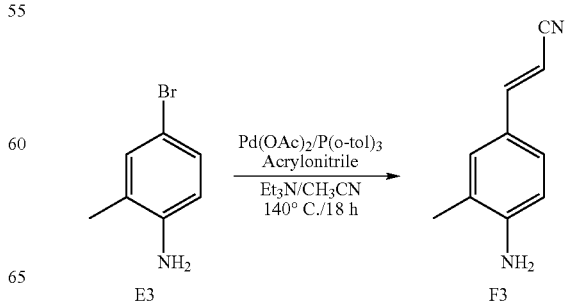

A mixture of 4-bromo-2-methylaniline (0.0268 mol), intermediate E3, palladium (0) acetate (0.00537 mol), tri-o-tolylphosphine (0.0268 mol) and acrylonitrile (0.0896 mol) in triethylamine (0.107 mol) and acetonitrile (70 ml) was stirred at 140° C. in a stainless-steel bomb for 18 h. After cooling, the mixture was filtered over celite and the filtrate was poured in water and extracted with CH₂Cl₂. The organic layer was dried over magnesium sulfate, filtered and the solvent evaporated. The residue was purified by column chromatography over silica gel (eluent: CH₂Cl₂/Cyclohexane 50/50; 35-70 μm). The pure fractions were collected and the solvent evaporated. Yield: 3.2 g of intermediate F3 (75%, melting point: 105° C.)

Preparation of Intermediates F4 and F6

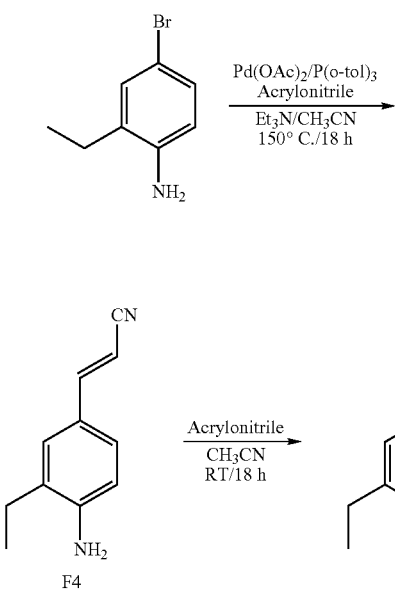

Intermediate F4 was prepared as described above for the preparation F3, using 4-bromo-2-ethylaniline as starting material. In a second step, N-bromosuccinimide (0.015 mol) was added portionwise to a mixture of 4-acrylonitrile-2-ethylaniline F4 (0.012 mol) in acetonitrile (25 ml). The mixture was stirred at room temperature overnight then poured in a mixture of water and K₂CO₃ 10%. The mixture was extracted with CH₂Cl₂. The organic layer was dried over magnesium sulfate, filtered and the solvent evaporated. The residue was purified by column chromatography over silica gel (eluent: Cyclohexane/ethyl acetate 90/10; 15-40 μm). The pure fractions were collected and the solvent evaporated. Yield: 0.75 g of intermediate F6 (26%).

Example 4

Preparation of Intermediates H, I and J

Preparation of Intermediate H

A mixture of 2,4-dichloro-5-nitro-pyrimidine (0.0516 mol) and 4-(2-cyanoethenyl)-2,6-dimethylphenylamine (0.0516 mol) was stirred at 140° C. in an oil bath for 45 minutes, then poured in a mixture of water and K$_2$CO$_3$ 10%. The precipitate was filtered and the filtrate extracted with CH$_2$Cl$_2$. The organic layer was dried over magnesium sulfate, filtered and the solvent evaporated. The residue was purified by column chromatography over silica gel (eluent: CH$_2$Cl$_2$ 100; 35-70 μm). The pure fractions were collected and the solvent evaporated, yielding 6.0 g of intermediate H (35%, melting point: >250° C.).

Preparation of Intermediate I

A mixture of intermediate H (0.0182 mol) and 4-cyanoaniline (0.0182 mol) was heated at fusion for 5 minutes, then poured in a mixture of water and K$_2$CO$_3$ 10%. CH$_2$Cl$_2$ and a small quantity of MeOH were added and the precipitate was filtered and dried, yielding 7.4 g of intermediate I (95%, melting point: >250° C.).

Preparation of Intermediate J

A mixture of intermediate I (0.0180 mol) and tin (II) chloride dihydrate (0.125 mol) in ethanol (100 ml) was stirred at 70° C. overnight, then poured in a mixture of water and K$_2$CO$_3$ 10%. The precipitate was filtered over celite. The filtrate was removed and the precipitate was washed with CH$_2$Cl$_2$ and THF. The solvent was evaporated. Yield: 6.0 g of intermediate J (87%, melting point: >250° C.).

Example 5

Preparation of Intermediates K, L and M
(6-chloro-2-fluorophenyl Analogs of Intermediates H, I and J)

A mixture of 2,4-dichloro-5-nitro-pyrimidine (0.0153 mol) and 4-(2-cyanoethenyl)-6-chloro-2-fluoro-phenylamine (0.0153 mol) was heated at fusion for 5 minutes, then poured in a mixture of water and K$_2$CO$_3$ 10% and extracted with CH$_2$Cl$_2$. The organic layer was dried over magnesium sulfate, filtered and the solvent evaporated. The residue was purified by column chromatography over silica gel (eluent: CH$_2$Cl$_2$ 100; 35-70 μm). The pure fractions were collected and the solvent evaporated. Yield: 1.9 g of 2-chloro-4-[4-(2-cyanoethenyl)-2-fluoro-6-chloro-phenylamino]-5-nitro-pyrimidine, intermediate K (35%, melting point: 217° C.).

A mixture of intermediate K (0.000424 mol) and 4-cyanoaniline (0.000424 mol) was heated at fusion for 5 minutes, then poured in a mixture of water and K$_2$CO$_3$ 10%. CH$_2$Cl$_2$ and a small quantity of MeOH was added and the precipitate was filtered and dried, yield: 1.34 g of 4-[4-[4-(2-cyanoethenyl)-2-fluoro-6-chloro-phenylamino]-5-nitro-pyrimidine]amino] benzonitrile, intermediate L (73%, melting point: >250° C.)

A mixture of intermediate L (0.00306 mol) and tin (II) chloride dihydrate (0.0214 mol) in ethanol (20 ml) was stirred at 70° C. overnight, then poured in a mixture of water and K$_2$CO$_3$ 10%. The precipitate was filtered over celite. The filtrate was removed and the precipitate was washed with CH$_2$Cl$_2$ and THF. The solvent was evaporated. Yield: 1.1 g of 4-[4-[4-(2-cyanoethenyl)-2-fluoro-6-chloro-phenylamino]-5-amino-pyrimidine]amino]benzonitrile, intermediate M (89%, melting point: >250° C.).

Example 6

Preparation of dihydro-pyrrolopyrimidine
Compound 1

A mixture of F3 (0.00126 mol) and D (0.00126 mol) was stirred at 180° C. in an oil bath for 20 hours, then poured in a mixture of water and K$_2$CO$_3$ 10% and extracted with CH$_2$Cl$_2$. The organic layer was dried over magnesium sulfate, filtered and the solvent evaporated. The residue was purified by column chromatography over silica gel (eluent: MeOH/AcNH$_4$/THF 40/40/20; Kromasil C18, 10 μm). The pure fractions were collected and the solvent evaporated. Yield: 0.18 g of compound 1 (E/Z: 95/5) and 0.124 g of compound 1 (E/Z: 65/35) (overall yield 61%, melting point (E/Z: 95/5): 244° C.).

Example 7

Preparation of dihydro-pyrrolopyrimidine Derivative 14

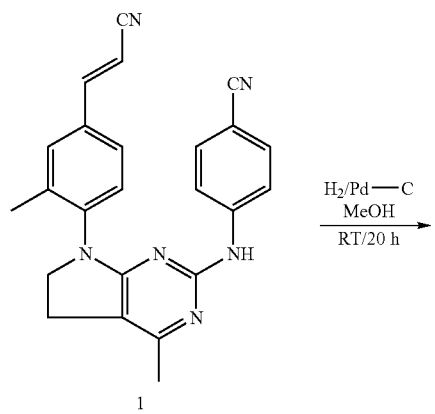

To a nitrogen flushed solution of 1 (0.00051 mol) in MeOH (20 ml), palladium on activated carbon 10% Pd (0.2 g, 10% wt) was added. The mixture was stirred at room temperature under 3 bars of hydrogen for 20 hours, then filtered over celite and the solvent was evaporated. The residue was crystallized from $CH_2Cl_2$/diisopropyl-ethylether. Yield: 0.05 g of compound 14 (25%, melting point: 195° C.).

Example 8

Preparation of pyrrolopyrimidine Derivative 28

2,3-Dichloro-5,6-dicyano-1,4-benzoquinone (0.00222 mol) was added to a mixture of compound 11 (0.000738 mol), prepared following similar procedures as in example 1, in 1,4-dioxane (10 ml). The mixture was stirred at reflux for 2 hours, then cooled and poured on ice. The precipitate was filtered and purified by column chromatography over silica gel (eluent: $CH_2Cl_2$/MeOH/$NH_4OH$ 98/2/0.1; 10 μm). The pure fractions were collected and the solvent evaporated. The residue was crystallized from diisopropyl-ethylether. Yield: 0.022 g of compound 28 (7%, melting point: 217° C.).

Example 9

Preparation of pyrrolopyrimidine Derivative 34

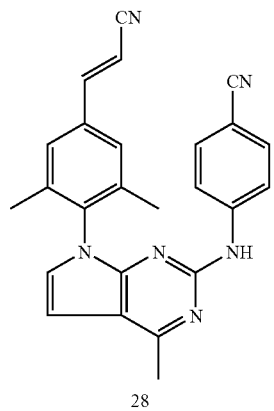

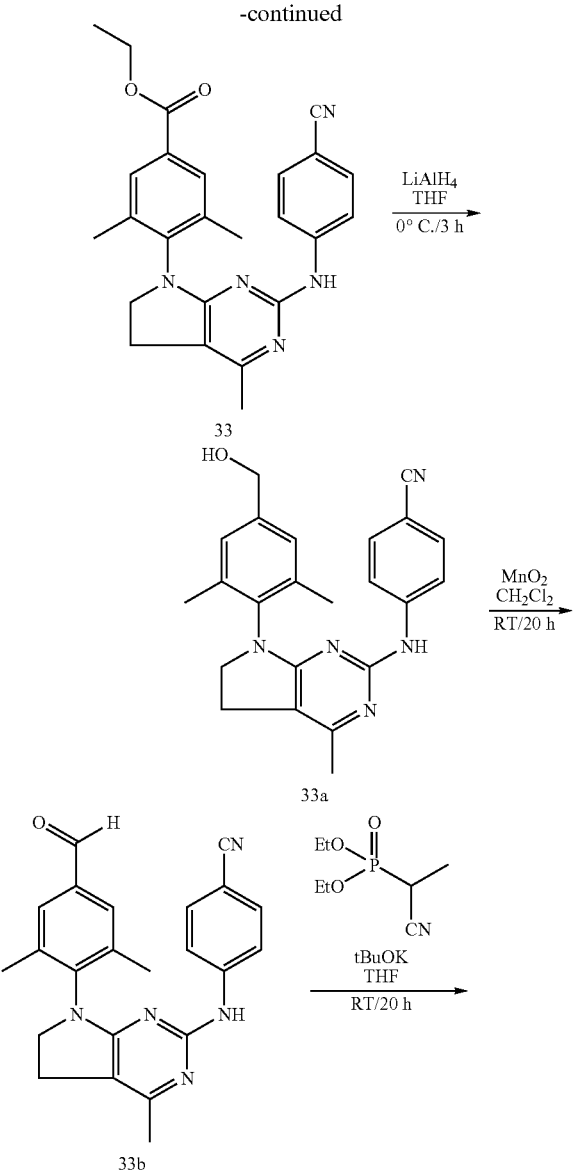

Preparation of dihydro-pyrrolopyrimidine Compound 33

A mixture of ethyl 4-amino-3,5-dimethylbenzoate G (0.0155 mol) and D (0.0155 mol) was stirred at 180° C. in an oil bath for 20 hours, then poured in a mixture of water and K₂CO₃ 10% and extracted with CH₂Cl₂. The organic layer was dried over magnesium sulfate, filtered and the solvent evaporated. The residue was purified by column chromatography over silica gel (eluent: CH₂Cl₂; 70-200 μm). The pure fractions were collected and the solvent evaporated. Yield: 2.2 g of compound 33 (33%, melting point: 92° C.).

Preparation of dihydro-pyrrolopyrimidine Derivative 33a

Compound 33 (0.00234 mol) was added portion wise to a mixture of lithium aluminum hydride (0.00702 mol) in THF (15 ml) at 0° C. The mixture was stirred at room temperature for 3 hours. Ethyl acetate was added, then water and the mixture was extracted with ethyl acetate. The organic layer was dried over magnesium sulfate, filtered and the solvent was evaporated. The residue was engaged in the next step with no further purification.

Preparation of dihydro-pyrrolopyrimidine Derivative 33b

To the residue of compound 33a (0.860 g) in CH₂Cl₂ was added manganese (IV) oxide (0.0104 mol) and the mixture was stirred at room temperature for 20 hours. After filtration over celite, the solvent was evaporated. The residue was purified by column chromatography over silica gel (eluent: CH₂Cl₂; 70-200 μm). The pure fractions were collected and the solvent evaporated. Yield: 0.160 g of compound 33b (18% for the two steps, melting point: oil).

Preparation of dihydro-pyrrolopyrimidine Compound 34

To a mixture of diethyl-(1-cyanoethyl)-phosphonate (0.000782 mol) in THF (5 ml) was added at 0° C. under nitrogen potassium tert-butoxide (0.000782 mol) and the mixture was stirred at room temperature for 1 hour. Compound 33b (0.000261 mol) was added and the mixture was stirred at room temperature for 20 hours, then poured in water and extracted with CH₂Cl₂. The organic layer was dried over magnesium sulfate, filtered and the solvent was evaporated. The residue was purified by column chromatography over silica gel (eluent: CH₂Cl₂; 35-70 μm). The pure fractions were collected and the solvent evaporated. The residue was crystallized from diisopropyl-ethylether. Yield: 0.075 g of compound 34 (E/Z: 50/50) (68%, melting point: 105° C.).

Example 10

Preparation of Compound 20

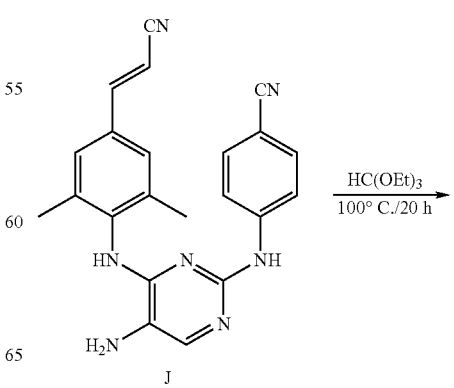

53

-continued

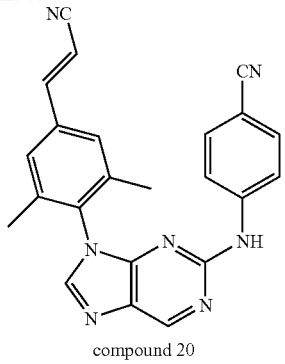

compound 20

A mixture of J (0.000524 mol) and triethyl orthoformate (5 ml) was stirred at 100° C. for 20 hours. After cooling, water and K$_2$CO$_3$ 10% was added. The precipitate was filtered off and dried. Yield: 0.155 g of compound 20 (76%, melting point >250° C.).

Example 11

Preparation of Compound 21

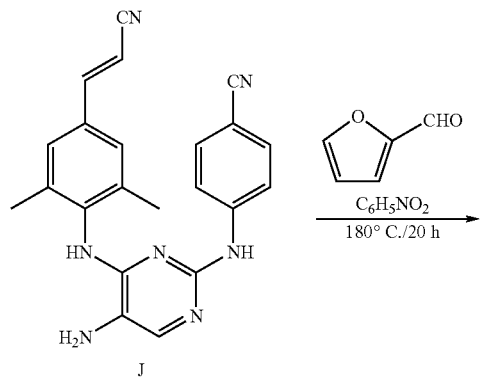

compound 21

A mixture of J (0.000524 mol) and 2-furaldehyde (0.00524 mol) in nitrobenzene (5 ml) was stirred at 180° C. for 20 hours. After cooling, the residue was filtered over silica gel to eliminate nitrobenzene. The solvent was evaporated and the residue was purified by column chromatography over silica gel (eluent: CH$_2$Cl$_2$/MeOH/NH$_4$OH 99/1/0.1; 10 µm). The pure fractions were collected and the solvent evaporated. The

54 residue was crystallized from diisopropyl-ethylether. Yield: 0.055 g of compound 21 (23%, melting point: 236° C.).

Example 12

Preparation of Compound 29 (triazolo derivative)

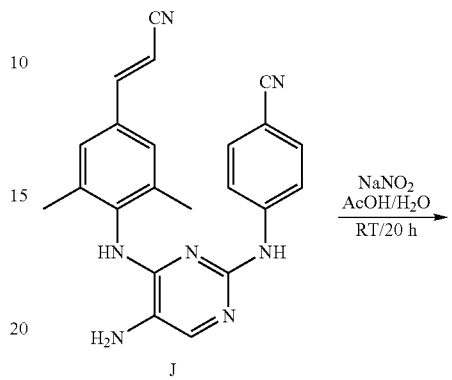

Sodium nitrite (0.000629 mol) in water (2 ml) was slowly added at 0° C. to a mixture of J (0.000524 mol) in water (2.5 ml) and acetic acid (1.5 ml). The mixture was stirred at room temperature for 5 hours. The precipitate was filtered, washed with water and diisopropyl-ethylether and dried. Yield: 0.110 g of compound 29 (53%, melting point >250° C.).

Example 13

Preparation of Compound 30

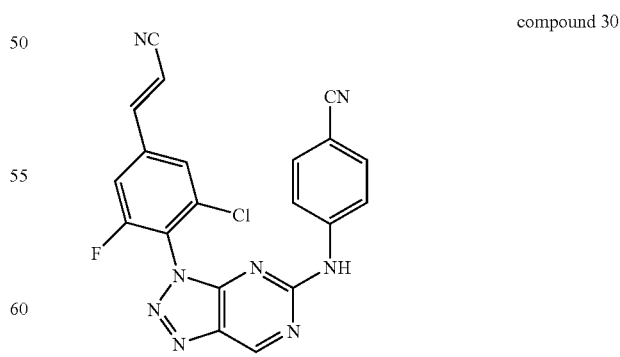

compound 30

The same procedure as in example 12 was used for the preparation of this derivative starting with 0.000370 mol of J analog and 0.000444 mol of sodium nitrite. Yield: 0.065 g of compound 30 (42%, melting point >250° C.).

Example 14

Preparation of Compound 31

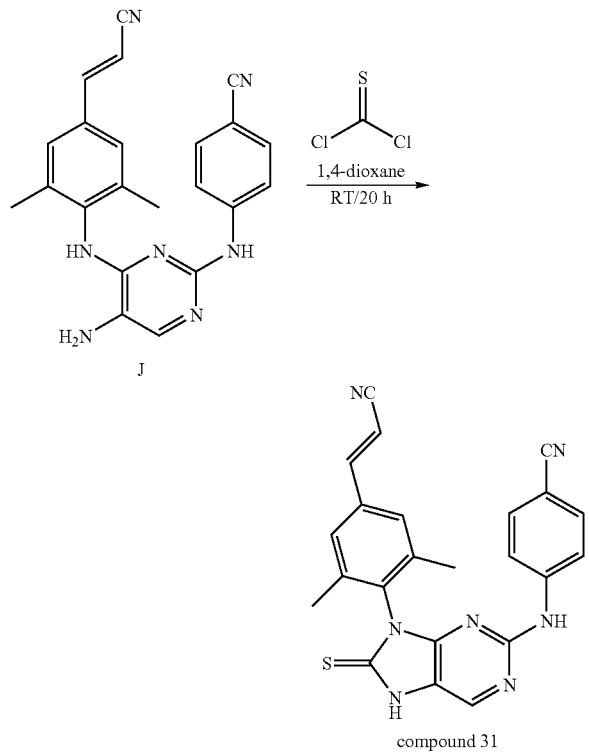

compound 31

Thiophosgene (0.000786 mol) was slowly added dropwise at 0° C. to a mixture of J (0.000524 mol) in 1,4-dioxane (5 ml). The mixture was stirred at room temperature for 4 hours and thiophosgene was added (0.000393 mol) and the mixture was stirred overnight. NH$_4$OH was slowly added at 0° C. and the mixture was extracted with CH$_2$Cl$_2$. The organic layer was dried over magnesium sulfate, filtered and the solvent evaporated. Yield: 0.105 g of compound 31 (47%, melting point >250° C.)

Example 15

Preparation of Compound 32

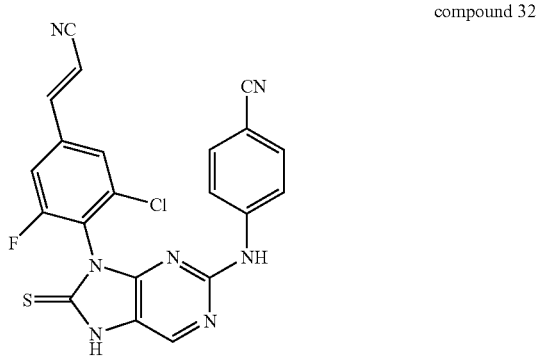

compound 32

The same procedure as in example 14 was used for the preparation of compound 32, starting with 0.000370 mol of intermediate M and 0.000554 mol of thiophosgene. Yield: 0.140 g of compound 32 (85%, melting point >250° C.).

Example 16

Preparation of Compound 26

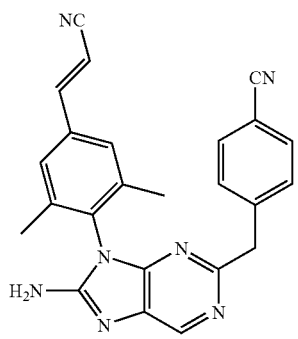

compound 26

Cyanogen bromide (0.000793 mol) was added portion wise at room temperature to intermediate J (0.000524 mol) in EtOH (6 ml) and THF (5 ml). The mixture was stirred at room temperature overnight. Cyanogen bromide (0.000264 mol) was added and the mixture was stirred at room temperature one day. The mixture was poured in a mixture of water and K$_2$CO$_3$ 10% and extracted with CH$_2$Cl$_2$. The organic layer was dried over magnesium sulfate, filtered and the solvent evaporated. The residue was crystallized from CH$_2$Cl$_2$. Yield: 0.092 g of 26 (43%, melting point: >250° C.).

Tables 1-6 list intermediates and compounds that were prepared according to one of the above Examples (Ex. No.).

TABLE 1

| Comp. Nr. | Ex. No. | R$^1$ | R$^2$ | Phys. Data |
|---|---|---|---|---|
| F1 | 3 | F | F | 168° C. |
| F2 | 3 | Et | Et | 69° C. |
| F3 | 3 | Me | H | 105° C. |
| F4 | 3 | Et | H | Oil |
| F5 | 3 | F | H | 99° C. |
| F6 | 3 | Et | Br | 75° C. |
| F7 | 3 | Me | Br | 87° C. |
| F8 | 3 | Cl | Cl | 131° C. |
| F9 | 2 + 3 | F | Cl | 144° C. |
| F10 | 3 | OMe | Me | 110° C. |

TABLE 2

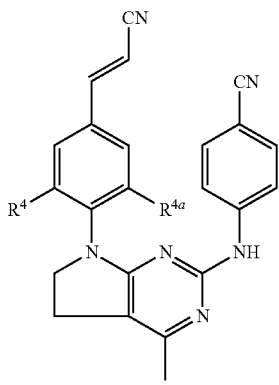

| Comp. Nr. | Ex. No. | R⁴ | R⁴ᵃ | Phys. Data and stereochemistry |
|---|---|---|---|---|
| 1 | 6 | Me | H | (E/Z:95/5); 244° C. |
| 2 | 6 | F | F | (E/Z:95/5); >250° C. |
| 3 | 6 | Et | Et | (E/Z:95/5); 139° C. |
| 4 | 6 | Et | H | (E); 210° C. |
| 5 | 6 | F | H | (E/Z:94/6); >250° C. |
| 6 | 6 | Et | Br | (E/Z:98/2); 146° C. |
| 7a | 6 | Cl | Cl | (E/Z:97/3); 151° C. |
| 7b | 6 | Cl | Cl | (E/Z:88/12) |
| 8 | 6 | OMe | Me | (E); >250° C. |
| 9 | 6 | Me | Br | (E/Z:85/15); 130° C. |
| 10 | 6 | F | Cl | (E); 138° C. |
| 11 | 6 | Me | Me | (E/Z:83/17); 215° C. |
| 12 | 6 | F | F | (Z); >250° C. |
| 13 | 6 | F | Cl | (Z); >250° C. |

TABLE 3

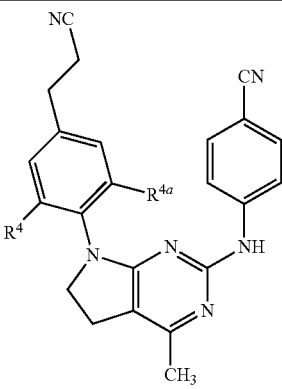

| Comp. Nr. | Ex. No. | R⁴ | R⁴ᵃ | Phys. Data |
|---|---|---|---|---|
| 14 | 7 | Me | H | 195° C. |
| 15 | 7 | Me | Me | 195° C. |
| 16 | 7 | Et | Et | 68-70° C. |
| 17 | 7 | Et | H | 176° C. |
| 18 | 7 | F | H | 189° C. |
| 19 | 7 | F | F | 191° C. |

TABLE 4

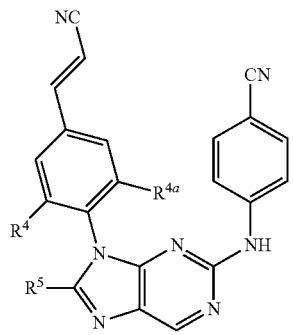

| Comp. No. | Ex. No. | R⁴ | R⁴ᵃ | R⁵ | Phys. Data and stereochemistry |
|---|---|---|---|---|---|
| 20 | 10 | Me | Me | H | (E); >250° C. |
| 21 | 11 | Me | Me | 2-furyl | (E); 236° C. |
| 22 | 11 | Me | Me | ethyl | (E); >250° C. |
| 23 | 11 | Me | Me | phenyl | (E); >250° C. |
| 24 | 11 | F | Cl | H | (E/Z:93/7); >250° C. |
| 25 | 11 | Me | Me | 2-pyridyl | (E); 231° C. |
| 26 | 16 | Me | Me | NH₂ | (E); >250° C. |
| 27 | 16 | F | Cl | NH₂ | (E); >250° C. |

TABLE 5

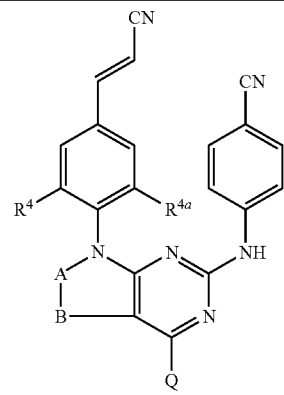

| Comp. Nr. | Ex. No. | A-B | R⁴ | R⁴ᵃ | Q | Phys. Data and stereochemistry |
|---|---|---|---|---|---|---|
| 28 | 8 | —CH=CH— | Me | Me | Me | 217° C. |
| 29 | 12 | —N=N— | Me | Me | H | (E); >250° C. |
| 30 | 13 | —N=N— | F | Cl | H | (E); >250° C. |
| 31 | 14 | —C(=S)—NH— | Me | Me | H | (E/Z): 98/2; >250° C. |
| 32 | 15 | —C(=S)—NH— | F | Cl | H | (E/Z):93/7; >250° C. |

TABLE 6

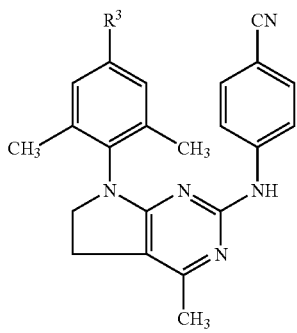

| Comp. Nr. | Ex. No. | R³ | Phys. Data and stereochemistry |
|---|---|---|---|
| 33 | 9 | —COOEt | 92° C. |
| 34 | 9 | —CH=C(CH₃)CN | (E/Z):50/50; 105° C. |

Formulation Examples

Capsules

A compound of formula (I) is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropyl-methylcellulose (HPMC), typically 5 mPa·s, are dissolved in organic solvents such as ethanol, methanol methylene chloride. Suitably the polymer is dissolved in ethanol. The polymer and compound solutions are mixed and subsequently spray dried. The ratio of compound/polymer is selected from 1/1 to 1/6. Intermediate ranges can be 1/1.5 and 1/3. A suitable ratio can be 1/6. The spray-dried powder, a solid dispersion, is subsequently filled in capsules for administration. The drug load in one capsule ranges between 50 and 100 mg depending on the capsule size used.

Film-Coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenized. The tablet cores are coated with the thus obtained mixture in a coating apparatus.

Antiviral Spectrum

Because of the increasing emergence of drug resistant HIV strains, the present compounds were tested for their potency against clinically isolated HIV strains harboring several mutations. These mutations are associated with resistance to reverse transcriptase inhibitors and result in viruses that show various degrees of phenotypic cross-resistance to the currently commercially available drugs such as for instance AZT and delavirdine. The antiviral activity of the compound of the present invention has been evaluated in the presence of wild type HIV and HIV mutants bearing mutations at the reverse transcriptase gene. The activity of the compounds is evaluated using a cellular assay and the residual activity is expressed in $pEC_{50}$ values. The columns IIIB and A-G in the table list the $pEC_{50}$ values against various strains IIIB, A-G.

Strain IIIB is wild type HIV-LAI strain

Strain A contains mutation Y181C in HIV reverse transcriptase,

Strain B contains mutation K103N in HIV reverse transcriptase,

Strain C contains mutation L100I in HIV reverse transcriptase,

Strain D contains mutation Y188L in HIV reverse transcriptase,

Strain E contains mutations L100I and K103N in HIV reverse transcriptase,

Strain F contains mutations K103N and Y181C in HIV reverse transcriptase, and

Strain G contains mutations L100I, K103N, Y181C, V179I, E138G, L214F, V278V/I and A327A/V in HIV reverse transcriptase.

| Comp. number | IIIB | A | B | C | D | E | F | G |
|---|---|---|---|---|---|---|---|---|
| 1 | 8.4 | 7.9 | 9 | 8.9 | 7.7 | 7.8 | 7.1 | 5.5 |
| 2 | 9.1 | 7.9 | 9.2 | 9.3 | 8.4 | 9.1 | 7.4 | 5.7 |
| 3 | 7.9 | 7.8 | 8.5 | 8.7 | 7.8 | 8.5 | 7.7 | 5.7 |
| 4 | 8.4 | 8.3 | 9 | 9 | 7.9 | 8.1 | 7.6 | 5.1 |
| 5 | 7.7 | 6.3 | 7.9 | 7.8 | 6.6 | 6.9 | — | <4.6 |
| 6 | 8.3 | 7.7 | 8.3 | 8.4 | 7.5 | 8.3 | 7.5 | 5.5 |
| 7a | 8.7 | 7.9 | 8.7 | 9.1 | 7.7 | 8.6 | 7.7 | 5.4 |
| 7b | 9.1 | 8.1 | 9 | 9.1 | 7.7 | 8.5 | 7.7 | 5.4 |
| 8 | 8.5 | 7.6 | 8.4 | 8.3 | 7.5 | 7.6 | 7.2 | 4.9 |
| 9 | 8.9 | 8.3 | 8.4 | 8.7 | 8.4 | 7.8 | 7.7 | <4.6 |
| 10 | 9.2 | 8.4 | 9.1 | 9.2 | 8 | 8.7 | 7.9 | 5.7 |
| 11 | 8.8 | 8.2 | 9 | 8.8 | 8.1 | 8.4 | 7.9 | 5.4 |
| 13 | 8.4 | 7.1 | 8.4 | 8.4 | 7 | 7.8 | 7 | 5.1 |
| 14 | 8.9 | 7.8 | 8.5 | 8.4 | 7 | 7.2 | 6.9 | 5.5 |
| 15 | 9 | 8.2 | 8.6 | — | 7.3 | 8 | 8 | 5.7 |
| 16 | 8.2 | 7.7 | 8.2 | 8.6 | 7 | 8.1 | 7.3 | 5.8 |
| 17 | 9 | 8.2 | 8.9 | 8.6 | 7.7 | 7.8 | 7.2 | 5.7 |
| 20 | 9.7 | 8.6 | 9.2 | 9.2 | 7.8 | 8.1 | 7.4 | 5.7 |
| 22 | 8.4 | 6.5 | 8.4 | 6.5 | 5.8 | 5.5 | 5.8 | — |
| 23 | 7.7 | 7.1 | 7.6 | 7.5 | 7.7 | 6.3 | 6.4 | 5.7 |
| 24 | 10 | 8.5 | 10 | 9.7 | 7.9 | 8.2 | 7.9 | 5.7 |
| 25 | 8.1 | 7.5 | 7.6 | 7.2 | 7.5 | 5.9 | 7.2 | 5.6 |
| 26 | 8.6 | 7.6 | 7.9 | 7.7 | 7.1 | 6.9 | 7.2 | 4.9 |
| 27 | 7.7 | 7.1 | — | 7.1 | 6.3 | 6.2 | 6.7 | 5.2 |
| 28 | 8.5 | 7.9 | 8.5 | 8.6 | 7.7 | 8.5 | 7.8 | 5.7 |
| 29 | 9.1 | 7.8 | 8.8 | 8.3 | 7.7 | 7.1 | — | 5.4 |
| 31 | 9 | 7.9 | 8.6 | 8.6 | 7.1 | 6.4 | 7.4 | 4.8 |
| 33 | 7.3 | 5.6 | 6.9 | 6.1 | 6.2 | 5.4 | 5.5 | 4.9 |
| 34 | 8.7 | 7.8 | 8.6 | 8.4 | 7.7 | 7.8 | 7.7 | 5.4 |

The invention claimed is:
1. A compound of formula

(I)

a N-oxide; a pharmaceutically acceptable addition salt; a quaternary amine; or a stereochemically isomeric form thereof, wherein -$a^1$=$a^2$-$a^3$=$a^4$- represents a bivalent radical of formula —CH=CH—CH=CH—     (a-1);

—N=CH—CH=CH—     (a-2);

—N=CH—N=CH—     (a-3);

—N=CH—CH=N—     (a-4); or

—N=N—CH=CH—     (a-5);

-$b^1$=$b^2$-$b^3$=$b^4$- represents a bivalent radical of formula

—CH=CH—CH=CH—     (b-1);

—N=CH—CH=CH—     (b-2);

—N=CH—N=CH—     (b-3);

—N=CH—CH=N—     (b-4); or

—N=N—CH=CH—     (b-5);

n is 0, 1, 2, 3 and in case -$a^1$=$a^2$-$a^3$=$a^4$- is (a-1), then n may also be 4;

m is 0, 1, 2, 3 and in case -$b^1$=$b^2$-$b^3$=$b^4$- is (b-1), then m may also be 4;

-A-B— represents a bivalent radical of formula

—$CR^5$=N—     (c-1);

$R^1$ is hydrogen; aryl; formyl; $C_{1-6}$alkylcarbonyl; $C_{1-6}$alkyl; $C_{1-6}$alkyloxycarbonyl; or $C_{1-6}$alkyl substituted with formyl, $C_{1-6}$alkylcarbonyl, or with $C_{1-6}$alkyloxycarbonyl;

each $R^2$ independently is hydroxy; halo; $C_{1-6}$alkyl optionally substituted with one, two or three substituents each independently selected from halo, cyano and —C(=O)$R^6$; $C_{3-7}$cycloalkyl; $C_{2-6}$alkenyl optionally substituted with one, two or three substituents selected from halo, cyano and —C(=O)$R^6$; $C_{2-6}$alkynyl optionally substituted with one, two or three substituents each independently selected from halo, cyano and —C(=O)$R^6$; $C_{1-6}$alkyloxycarbonyl; carboxyl; cyano; nitro; amino; mono- and di($C_{1-6}$alkyl)amino; polyhalomethyl; polyhalomethylthio; —S(=O)$_p$$R^6$; —NH—S(=O)$_p$$R^6$; —C(=O)$R^6$; —NHC(=O)H; —C(=O)NHNH$_2$; NHC(=O)$R^6$; or C(=NH)$R^6$;

$R^{2a}$ is cyano; aminocarbonyl; amino; halo; $C_{1-6}$alkyloxy wherein the $C_{1-6}$alkyl moiety of the $C_{1-6}$alkyloxy is substituted with cyano; $NHR^{13}$; $NR^{13}R^{14}$; —C(=O)— $NHR^{13}$; —C(=O)—$NR^{13}R^{14}$; —C(=O)—$R^{15}$; —CH=N—NH—C(=O)—$R^{16}$; $C_{1-6}$alkyl substituted with one, two or three substituents each independently selected from halo, cyano, $NR^9R^{10}$, —C(=O)—$NR^9R^{10}$, —C(=O)—$C_{1-6}$alkyl and $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl and $R^7$; $C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl and $R^7$; $C_{2-6}$alkenyl substituted with one, two or three substituents each independently selected from halo, cyano, $NR^9R^{10}$, —C(=O)—$NR^9R^{10}$, —C(=O)—$C_{1-6}$alkyl and $R^7$; $C_{2-6}$alkynyl substituted with one, two or three substituents each independently selected from halo, cyano, $NR^9R^{10}$, —C(=O)—$NR^9R^{10}$, —C(=O)—$C_{1-6}$alkyl and $R^7$; —C(=N—O—$R^8$)—$C_{1-4}$alkyl; $R^7$ or —X—$R^7$;

$R^3$ is cyano; aminocarbonyl; amino; $C_{1-6}$alkyl; halo; $C_{1-6}$alkyloxy wherein the $C_{1-6}$alkyl moiety of the $C_{1-6}$alkyloxy may optionally be substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one, two or three substituents each independently selected from halo, cyano, $NR^9R^{10}$, —C(=O)—$NR^9R^{10}$, —C(=O)—$C_{1-6}$alkyl and $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl and $R^7$; $C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl and $R^7$; $C_{2-6}$alkenyl substituted with one, two or three substituents each independently selected from halo, cyano, $NR^9R^{10}$, —C(=O)—$NR^9R^{10}$, —C(=O)—$C_{1-6}$alkyl and $R^7$; $C_{2-6}$alkynyl substituted with one, two or three substituents each independently selected from halo, cyano, $NR^9R^{10}$, —C(=O)—$NR^9R^{10}$, —C(=O)—$C_{1-6}$alkyl and $R^7$; —C(=N—O—$R^8$)—$C_{1-4}$alkyl; $R^7$ or —X—$R^7$;

X is —$NR^1$—, —O—, —C(=O)—, —S—, or —S(=O)$_p$—;

each $R^4$ independently is halo; hydroxy; $C_{1-6}$alkyl optionally substituted with one, two or three substituents each independently selected from halo, cyano and —C(=O)$R^6$; $C_{2-6}$alkenyl optionally substituted with one, two or three substituents each independently selected from halo, cyano and —C(=O)$R^6$; $C_{2-6}$alkynyl optionally substituted with one, two or three substituents each independently selected from halo, cyano and —C(=O)$R^6$; $C_{3-7}$cycloalkyl; $C_{1-6}$alkyloxy; cyano; nitro; polyhalo$C_{1-6}$ alkyl; polyhalo$C_{1-6}$alkyloxy; aminocarbonyl; mono- or di($C_{1-4}$alkyl)aminocarbonyl; $C_{1-6}$alkyloxycarbonyl; $C_{1-6}$alkylcarbonyl; formyl; amino; mono- or di($C_{1-4}$ alkyl)amino or $R^7$;

Q is hydrogen, $C_{1-6}$alkyl, halo, polyhalo$C_{1-6}$alkyl, or —$NR^9R^{10}$;

$R^5$ is hydrogen, $C_{1-6}$alkyl, aryl, pyridyl, thienyl, furanyl, amino, mono- or di($C_{1-4}$alkyl)amino;

$R^6$ is $C_{1-4}$alkyl, amino, mono- or di($C_{1-4}$alkyl)amino or polyhalo$C_{1-4}$alkyl;

$R^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy $C_{1-6}$alkyl, amino$C_{1-6}$alkyl, mono and di($C_{1-6}$alkyl)amino $C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$), $R^{7a}$, —X—$R^{7a}$ and $R^{7a}$—$C_{1-4}$alkyl;

$R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino $C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, and —CH(=N—O—$R^8$);

$R^8$ is hydrogen, $C_{1-4}$alkyl, aryl or aryl$C_{1-4}$alkyl;

$R^9$ and $R^{10}$ each independently are hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; —CH(=N$R^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- and di($C_{1-4}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$, $R^7$; or $R^9$ and $R^{10}$ may be taken together to form a bivalent or trivalent radical of formula —CH$_2$—CH$_2$—CH$_2$—CH$_2$— (d-1);

—CH$_2$—CH$_2$—CH$_2$—CH$_2$—CH$_2$— (d-2);

—CH$_2$—CH$_2$—O—CH$_2$—CH$_2$— (d-3);

—CH$_2$—CH$_2$—S—CH$_2$—CH$_2$— (d-4);

—CH$_2$—CH$_2$—NR$^{12}$—CH$_2$—CH$_2$— (d-5);

—CH$_2$—CH=CH—CH$_2$— (d-6); or

=CH—CH=CH—CH=CH— (d-7);

$R^{11}$ is cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

$R^{12}$ is hydrogen or $C_{1-4}$alkyl;

$R^{13}$ and $R^{14}$ each independently are $C_{1-6}$alkyl optionally substituted with cyano or aminocarbonyl, $C_{2-6}$alkenyl optionally substituted with cyano or aminocarbonyl, or $C_{2-6}$alkynyl optionally substituted with cyano or aminocarbonyl;

$R^{15}$ is $C_{1-6}$alkyl substituted with cyano or aminocarbonyl;

$R^{16}$ is $C_{1-6}$alkyl optionally substituted with cyano or aminocarbonyl, or $R^7$;

each p is 1 or 2;

each aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, a radical Het and —X-Het; and Het is pyridyl, thienyl, furanyl, oxazolyl, isoxazolyl, imidazolyl, pyrazolyl, thiazolyl, thiadiazolyl, oxadiazolyl quinolinyl, benzothienyl, or benzofuranyl; which each may optionally be substituted with one or two $C_{1-4}$alkyl radicals.

2. A compound according to claim 1, wherein
-$a^1$=$a^2$-$a^3$=$a^4$- represents a bivalent radical of formula
—CH=CH—CH=CH— (a-1);
-$b^1$=$b^2$-$b^3$=$b^4$- represents a bivalent radical of formula
—CH=CH—CH=CH— (b-1);
n is 0, 1 or 2;
m is 0, 1 or 2; and
$R^1$ is hydrogen; formyl; $C_{1-6}$alkylcarbonyl; $C_{1-6}$alkyl; or $C_{1-6}$alkyloxycarbonyl.

3. A compound according to claim 1, wherein the compound has the formula

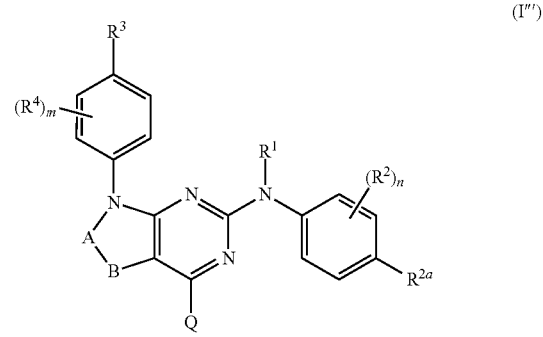

(I''')

wherein $R^1$, $R^2$, $R^{2a}$, $R^3$, $R^4$, -A-B—, m, n and Q are as defined in claim 1.

4. A compound according to claim 1, wherein the compound has the formula

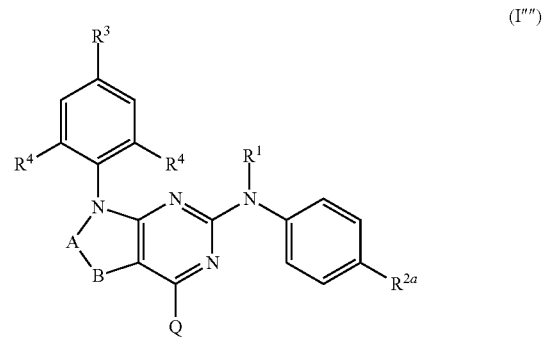

(I'''')

wherein $R^1$, $R^{2a}$, $R^3$, $R^4$, -A-B— and Q are as defined in claim 1.

5. A compound according to claim 1, wherein
$R^2$ is hydroxy; halo; $C_{1-6}$alkyl optionally substituted with one substituent selected from halo, cyano and —C(=O)

$R^6$; $C_{2-6}$alkenyl optionally substituted with one substituent selected from halo, cyano or —C(=O)$R^6$; $C_{2-6}$alkynyl optionally substituted with one substituent selected from halo, cyano or —C(=O)$R^6$; $C_{1-6}$alkyloxycarbonyl; carboxyl; cyano; nitro; amino; mono- and di($C_{1-6}$alkyl)amino; or trifluoromethyl;

$R^{2a}$ is cyano; aminocarbonyl; amino; halo; $C_{1-6}$alkyloxy wherein the $C_{1-6}$alkyl moiety of the $C_{1-6}$alkyloxy is substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one substituent selected from halo, cyano, —C(=O)—$NR^9R^{10}$, and —C(=O)—$C_{1-6}$alkyl; $C_{1-6}$alkyl substituted with hydroxy and a second substituent selected from halo, cyano, —C(=O)—$NR^9R^{10}$, and —C(=O)—$C_{1-6}$alkyl; $C_{1-6}$alkyloxy$C_{1-6}$alkyl optionally substituted with one substituent selected from halo, cyano, —C(=O)—$NR^9R^{10}$, and —C(=O)—$C_{1-6}$alkyl; $C_{2-6}$alkenyl substituted with one substituent selected from halo, cyano, —C(=O)—$NR^9R^{10}$, and —C(=O)—$C_{1-6}$alkyl; or $C_{2-6}$alkynyl substituted with one substituent selected from halo, cyano, —C(=O)—$NR^9R^{10}$, and —C(=O)—$C_{1-6}$alkyl;

$R^3$ is cyano; aminocarbonyl; amino; $C_{1-6}$alkyl; halo; $C_{1-6}$alkyloxy wherein the $C_{1-6}$alkyl moiety of the $C_{1-6}$alkyloxy may optionally be substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one substituent selected from halo, cyano, and —C(=O)—$NR^9R^{10}$; $C_{1-6}$alkyl substituted with hydroxy and a second substituent selected from halo, cyano, and —C(=O)—$NR^9R^{10}$; $C_{1-6}$alkyloxy$C_{1-6}$alkyl optionally substituted with one substituent selected from halo, cyano, and —C(=O)—$NR^9R^{10}$; $C_{2-6}$alkenyl substituted with one substituent selected from halo, cyano, and —C(=O)—$NR^9R^{10}$; or $C_{2-6}$alkynyl substituted with one substituent selected from halo, cyano, and —C(=O)—$NR^9R^{10}$; and $R^4$ is halo; hydroxy; $C_{1-6}$alkyl optionally substituted with one substituent selected from halo, cyano and —C(=O)$R^6$; $C_{2-6}$alkenyl optionally substituted with one substituent selected from halo, cyano and —C(=O)$R^6$; $C_{2-6}$alkynyl optionally substituted with one substituent selected from halo, cyano and —C(=O)$R^6$; $C_{3-7}$cycloalkyl; $C_{1-6}$alkyloxy; cyano; nitro; polyhalo$C_{1-6}$alkyl; polyhalo$C_{1-6}$alkyloxy; aminocarbonyl; mono- or di($C_{1-4}$ alkyl)amino-carbonyl; $C_{1-6}$alkyloxycarbonyl; $C_{1-6}$alkylcarbonyl; formyl; amino; mono- or di($C_{1-4}$ alkyl)amino or $R^7$.

6. A compound according to claim 1, wherein $R^1$ is hydrogen.

7. A compound according to claim 1, wherein
$R^2$ is halo, cyano, aminocarbonyl, $C_{1-6}$alkyl, $C_{1-6}$alkyl substituted with cyano or $C_{2-6}$alkenyl substituted with cyano;
$R^{2a}$ is halo, cyano, aminocarbonyl, $C_{1-6}$alkyl substituted with cyano or aminocarbonyl, or $C_{2-6}$alkenyl substituted with cyano or aminocarbonyl;
$R^3$ is halo, cyano, aminocarbonyl, $C_{1-6}$alkyl substituted with cyano or aminocarbonyl, or $C_{2-6}$alkenyl substituted with cyano or aminocarbonyl;
$R^4$ is halo; hydroxy; $C_{1-6}$alkyl optionally substituted with cyano; $C_{2-6}$alkenyl optionally substituted with cyano; $C_{2-6}$alkynyl optionally substituted with cyano; $C_{1-6}$alkyloxy; cyano; nitro; trifluoromethyl; aminocarbonyl; mono- or di($C_{1-4}$alkyl)aminocarbonyl; $C_{1-6}$alkyloxycarbonyl; $C_{1-6}$alkylcarbonyl; formyl; amino; mono- or di($C_{1-4}$alkyl)amino; and Q is hydrogen, amino, mono- or di-$C_{1-4}$alkylamino.

8. A compound according to claim 1 wherein
n is 0;
m is 2;
$R^2$ is halo, cyano, aminocarbonyl, $C_{1-4}$alkyl substituted with cyano or $C_{2-4}$alkenyl substituted with cyano;
$R^{2a}$ is cyano, aminocarbonyl, $C_{1-6}$alkyl substituted with cyano or $C_{2-6}$alkenyl substituted with cyano;
$R^3$ is cyano, $C_{1-4}$alkyl substituted with cyano or $C_{2-4}$alkenyl substituted with cyano;
$R^4$ is halo, hydroxy, $C_{1-6}$alkyl, $C_{2-6}$alkenyl, $C_{2-6}$alkynyl, $C_{1-6}$alkyloxy, cyano, nitro, amino; and
Q is hydrogen.

9. A compound according to claim 1 wherein
$R^2$ is cyano, aminocarbonyl;
$R^{2a}$ is cyano, aminocarbonyl, $C_{1-4}$alkyl substituted with cyano or $C_{2-4}$alkenyl substituted with cyano;
$R^3$ is $C_{1-4}$alkyl substituted with cyano or $C_{2-4}$alkenyl substituted with cyano;
$R^4$ is halo, $C_{1-4}$alkyl, $C_{1-4}$alkyloxy; and
Q is hydrogen.

10. A compound according to claim 1 wherein
$R^{2a}$ is cyano; aminocarbonyl; amino; halo; $C_{1-6}$alkyloxy wherein the $C_{1-6}$alkyl moiety of the $C_{1-6}$alkyloxy is substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one, two or three substituents each independently selected from halo, cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl and $R^7$;

$C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl and $R^7$;

$C_{2-6}$alkenyl substituted with one, two or three substituents each independently selected from halo, cyano, $NR^9R^{10}$, —C(=O)—$NR^9R^{10}$, —C(=O)—$C_{1-6}$alkyl and $R^7$;

$C_{2-6}$alkynyl substituted with one, two or three substituents each independently selected from halo, cyano, $NR^9R^{10}$, —C(=O)—$NR^9R^{10}$, —C(=O)—$C_{1-6}$alkyl and $R^7$;

—C(=N—O—$R^8$)—$C_{1-4}$alkyl; $R^7$ and —X—$R^7$; and $R^3$ is cyano; aminocarbonyl; amino; halo; $C_{1-6}$alkyloxy wherein the $C_{1-6}$alkyl moiety of the $C_{1-6}$alkyloxy is substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one, two or three substituents each independently selected from halo, cyano, $NR^9R^{10}$, —C(=O)—$NR^9R^{10}$, —C(=O)—$C_{1-6}$alkyl and $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl and $R^7$;

$C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl and $R^7$;

C$_{2-6}$alkenyl substituted with one, two or three substituents each independently selected from halo, cyano, NR$^9$R$^{10}$, —C(=O)—NR$^9$R$^{10}$, —C(=O)—C$_{1-6}$alkyl and R$^7$;

C$_{2-6}$alkynyl substituted with one, two or three substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ and —X—R$^7$.

11. A compound according to claim 1 wherein

R$^{2a}$ is halo, cyano, aminocarbonyl, C$_{1-6}$alkyl substituted with cyano or aminocarbonyl, C$_{2-6}$alkenyl optionally substituted with cyano or aminocarbonyl; and R$^3$ is halo, cyano, aminocarbonyl, C$_{1-6}$alkyl optionally substituted with cyano or aminocarbonyl, C$_{2-6}$alkenyl optionally substituted with cyano or aminocarbonyl.

12. A compound according to claim 1 wherein

R$^{2a}$ is halo, cyano, aminocarbonyl, C$_{1-6}$alkyl substituted with cyano or aminocarbonyl, or C$_{2-6}$alkenyl substituted with cyano or aminocarbonyl; and R$^3$ is halo, cyano, aminocarbonyl, C$_{1-6}$alkyl substituted with cyano or aminocarbonyl, or C$_{2-6}$alkenyl substituted with cyano or aminocarbonyl.

13. A compound according to claim 1, wherein

R$^3$ is C$_{2-6}$alkyl substituted with cyano, or C$_{2-6}$alkenyl substituted with cyano.

14. A compound according to claim 12, wherein

R$^{2a}$ is cyano or aminocarbonyl.

15. A compound according to claim 14, wherein R$^{2a}$ is cyano.

16. A pharmaceutical composition comprising a pharmaceutically acceptable carrier and as active ingredient a therapeutically effective amount of a compound as claimed in claim 1.

17. A process for preparing a pharmaceutical composition, said process comprising mixing as an active ingredient a therapeutically effective amount of a compound as claimed in claim 1 with a pharmaceutically acceptable carrier.

18. A process for preparing a compound as claimed in claim 1, said process comprising:

(a) reacting an intermediate of formula (II-a) or (II-b) with an intermediate of formula (III-a) or (III-b), in a suitable solvent:

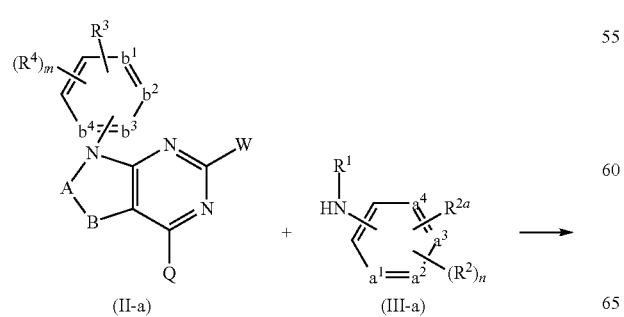

wherein each W independently represents a suitable leaving group;

(b) reacting the bicyclic derivative (IV) with an intermediate (V), in a suitable solvent:

-continued

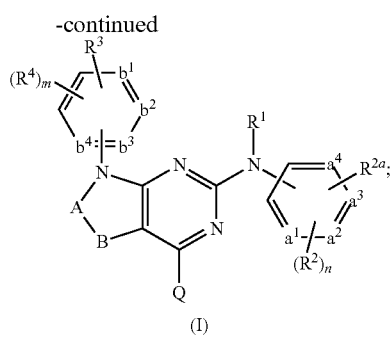

(I)

wherein W represents an appropriate leaving group;

(c) preparing compounds of formula (I-c) which are compounds of formula (I) wherein -A-B— is —CR$^5$═N— by reacting an aminopyrimidine (VIII) with an orthoformate R$^5$C(OEt)$_3$ or with an aldehyde R$^5$CH═O in the presence of a mild oxidant:

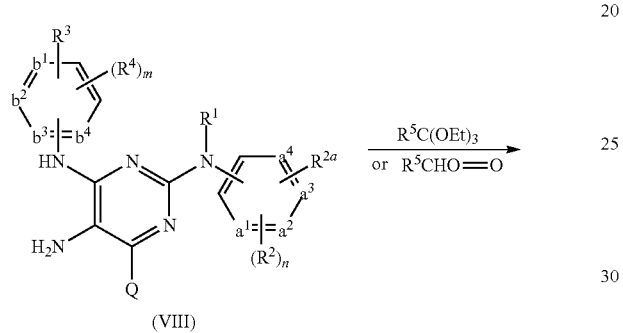

(VIII)

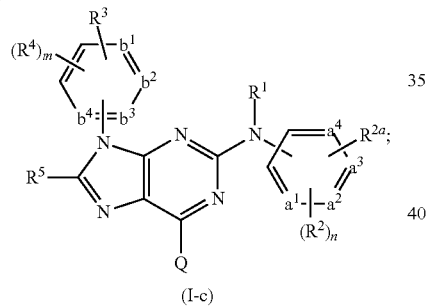

(I-c)

(d) preparing compounds of formula (I-c-1) which are compounds of formula (I) wherein -A-B— is —CR$^5$═N— wherein R$^5$ is amino, by reacting an aminopyrimidine (VIII) with a cyanogen halide, in a suitable solvent:

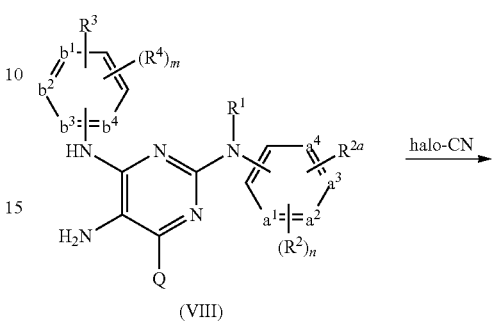

(VIII)

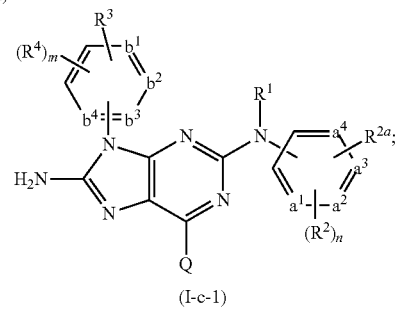

(I-c-1)

(e) mono- or bis-alkylating compounds of formula (I-c-1) to the corresponding compounds wherein R$^5$ is mono- or di(C$_{1-4}$alkyl)amino using a reagent C$_{1-4}$alkyl-W as alkylating agent;

(f) and if desired, preparing salt-forms by treating the free base or acid form of a compound of formula (I) with a suitable acid or base; or vice versa, preparing free base or acid forms by treating the salt forms of a compound of formula (I) with a suitable base or acid.

* * * * *